United States Patent [19]
Katzir et al.

[11] Patent Number: 5,834,203
[45] Date of Patent: Nov. 10, 1998

[54] METHOD FOR CLASSIFICATION OF PIXELS INTO GROUPS ACCORDING TO THEIR SPECTRA USING A PLURALITY OF WIDE BAND FILTERS AND HARDWIRE THEREFORE

[75] Inventors: Nir Katzir, Givat Elah; David Wine, Timrat; Yuval Garini, Koranit; Dario Cabib, Timrat, all of Israel

[73] Assignee: Applied Spectral Imaging, Migdal Haemek, Israel

[21] Appl. No.: 917,213

[22] Filed: Aug. 25, 1997

[51] Int. Cl.$^6$ .............................. C12Q 1/68; G02B 21/16; F21V 9/08
[52] U.S. Cl. ................................ 435/6; 359/368; 252/582
[58] Field of Search ................................ 435/6; 359/368; 252/582

[56] References Cited

PUBLICATIONS

Speicher et al, "Computer Image Analysis of Combinatorial Multi–Fluor FISH", *Bioimaging,* 4:52–64, 1996.
Veldman et al, "Hidden Chromosome Abnormalities in Haematological Malignancies Detected by Multicolor Spectral Karyotpying", *Nature Genetics,* 15: 406–410, 1997.

*Primary Examiner*—George C. Elliott
*Assistant Examiner*—John S. Brusca
*Attorney, Agent, or Firm*—Mark M. Friedman

[57] ABSTRACT

A method of classification of pixels into groups of pixels according to their association with a single fluorophore or a combination of fluorophores selected from a plurality of fluorophores, each of the fluorophores having characterizing excitation and emission spectra and specifying excitation and emission peaks, the method comprising the steps of (a) providing a plurality of pairs of wide-band excitation filters and wide-band emission filters; (b) exciting fluorophores of each of the pixels with light filtered through one of the wide-band excitation filters, and recording emitted light intensity as retrieved after passing through its paired emission filter; (c) repeating step (b) for all of the plurality of pairs of filters, such that each of the pixels is representable by a vector of a plurality of dimensions, the number of dimensions being equal to the number of the plurality of pairs of filters; (c) using an algorithm for evaluating the presence of each of the plurality of fluorophores in each of the pixels, thereby classifying each of the pixels into a group of pixels according to its association with a single fluorophore or combination of fluorophores.

49 Claims, 8 Drawing Sheets

METHOD FOR CLASSIFICATION OF PIXELS INTO GROUPS ACCORDING TO THEIR SPECTRA USING A PLURALITY OF WIDE BAND FILTERS AND HARDWIRE THEREFORE

FIELD AND BACKGROUND OF THE INVENTION

The present invention relates to classification of pixels into groups of pixels according to their spectra, as filtered through a plurality of wide band filters. The present invention further relates to determination of the amount of fluorophores present in a pixel. More particularly, the present invention relates to a method and apparatus (i) for classification of pixels presenting in situ fluorescently painted chromosomes into groups of pixels, each group is associated with genetic material derived from a different chromosome and (ii) for determining the amount of fluorophores present in any pixel thereof.

The use of fluorescent dyes (i.e., fluorescent probes, fluorophores, fluorochromes, all are used interchangeably in this document), is one of the most powerful and common tools for analyzing tissues and cells. Fluorescence microscopy is therefore one of the most important experimental methods used in light microscopy [Lakowicz (1983) Principles of fluorescence spectroscopy Plenum Press, New York, London].

The power of fluorescent probes, is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see. Mason, editor (1993) Fluorescent and Luminescent Probes for Biological Activity, Biological Techniques Series, edited by Sattelle, Academic Press Limited, London; and, Ploem and Tanke (1987) Introduction to Fluorescence Microscopy. Oxford University Press, Royal Microscopical Society.

The rapid development of new and more sophisticated multicolor fluorescent dye molecules continues to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

An important example, where the detection of multiple fluorescent probes can be a significant advantage is FISH (fluorescent in situ hybridization) [Emanuel (1993) Growth Genetics and Hormones 9, pp. 6–12], which is used to analyze genes at the chromosome level, and find possible genetic defects such as gene/chromosome amplification, deletion, translocation, rearrangement and other abnormalities.

Certain diseases and disorders, including many cancers and birth defects, are genetic disorders caused by defects (i.e., mutations) in one or more genes. Many other diseases are known or believed to have a genetic component(s), that is, there exists a genetic defect(s) that does not alone cause the disease but contributes to its development, or increases the probability of developing the disease later in life, phenomena known in the art as multifactorial diseases and genetic predispositions.

Correlation of visible genetic defects with known diseases would allow Doctors to make definitive diagnoses, and permit early detection and treatment of many diseases. Genetic counseling could alert prospective parents and at-risk individuals to the possibility of potentially serious medical problems in the future, permitting appropriate intervention.

More than 8,000 genetic disorders have now been identified, many of which are associated with multiple genetic defects. Following the discovery that chromosomes are the carriers of hereditary information, scientists reasoned that it should be possible to document visible defects in chromosomes that were responsible for specific disorders.

In the 1960's, staining techniques were developed for microscopy-based classification of metaphase chromosomes spread onto glass slides. For several decades, visual analysis of chromosomes banding patterns has been used to correlate human genetic disorders with observed structural abnormalities in metaphase chromosomes. Chromosomes are typically examined by brightfield microscopy after Giemsa staining (G-banding), or examined by fluorescence microscopy after fluorescence staining (R-banding), to reveal characteristic light and dark bands along their length. Careful comparison of a patient's banding pattern with those of normal chromosomes can reveal abnormalities such as translocations (exchange of genetic material between or within chromosomes). deletions (missing chromosome(s) or fragment(s) thereof), additions, inversions and other defects that cause deformities and genetic diseases. Yet conventional chromosome banding techniques are limited in resolution.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes.

The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (i) FISH can be used not only on isolated chromosomes and nucleus, but also whole cells within fixed paraffin-embedded tissue sections; (ii) it can detect relatively small defects (ability of detecting smaller defects constantly increases); (iii) it can provide results relatively fast; (iv) its moderate cost allows it to be used in most diagnostic and research laboratories; (v) adaptation can be developed for various probes and specimen types; and, (vi) high specificity and sensitivity can be achieved, within a short time, typically in the range of two hours.

Many FISH applications merely require from the cytogeneticist to look through the eyepieces of a microscope, or at the image on the monitor and to determine whether a fluorescent label is present or absent. With somewhat more complex specimens, a simple count of one or two colored labels may be done. However, the ability to process digital images and extract numerical data from them adds a vast new set of capabilities to FISH techniques.

An appropriate imaging method, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene.

As discussed above, FISH can provide information on the location of the labeled probe, the number of labeled sites on each chromosome, and the intensity of labeling (the amount of genetic material) at each site. Centromeric (repetitive DNA) probes and chromosome paints are used to tag and count the number of copies present of each targeted chromosome. Locus-specific probes are used to map the location of small regions of genetic material. These types of probes can be used on intact interphase nucleus as well as metaphase chromosome spreads and can be counted visually or automatically by a suitable algorithm. They are routinely used to identify genetic diseases characterized by having too many or too few copies of a specific chromosome, chromosome fragment, or gene.

In very early stages of some cancers, long before the cells are recognized as abnormal, there may be an increase in the number of specific genes, phenomenon known in the art as gene amplification, that are detectable using locus-specific probes as homogeneously stained regions (HSR) and/or double minute chromosomes. Using FISH to detect chromosome abnormalities in cancerous cells may point out the developmental stage the disease has reached and therefore to select the most suitable treatment(s), many of which are stage specific in their effectiveness. Thereby precious time is saved and patient's suffering is minimized, selecting the most effective stage specific treatment.

It is possible to uniformly label the entire surface of one specific chromosome by isolating the chromosome (using flow cytometry, for example), physically (e.g., by sonication) or enzymatically (e.g., by random or sequence specific endonucleases) chopping it up, and generating a set of probes against all of the fragments. Whole chromosome probes, also known as chromosome paints, fluorescently label all copies of their target chromosome. One important application of chromosome painting is the detection of translocations and insertions of genetic material between two chromosomes, as characteristically occurs in early stages of certain cancers, yet other chromosome aberrations are also detectable.

For example, if chromosome A is specifically labeled with a green paint and chromosome B is labeled with a red paint, any translocation of genetic material from A to B will appear as a green area on a red chromosome (and vice versa). Typically, chromosome paints generated from normal chromosomes are used to detect deletions or translocations of abnormal (patient) chromosomes. Reverse chromosome painting uses probes generated from an abnormal chromosome to identify DNA from various normal chromosomes which contributed material to the abnormal chromosome.

The method of the present invention, as exemplified hereinbelow in the Examples section, enables to paint the 24 different chromosomes comprising the human karyotype (i.e., genome) each in a different color and simultaneously detect identify and meaningfully display a color human karyotype, using a single hybridization followed by a single short measurement.

It will be easily recognized that this invention can be used in many other situations and applications, not related to chromosome analysis. For example, the method according to the present invention can be used in multiprobe immunohistochemistry, where many fluorescently labeled DNA and/or protein (antibodies) probes are introduced to cells for the detection and mapping of genes and proteins related to the onset and progression of cancer and other diseases.

A remarked improvement in multicolor fluorescent dyes used for labeling chromosome paints is the introduction of combinatorial fluorescent strategies (e.g., combinatorial labeling and combinatorial hybridization) which employ various combinations of few basic fluorescent dyes. For further details on combinatorial labeling see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein. For further details about combinatorial hybridization see du-Manoir et al. (1993) Detection of complete and partial chromosome gains and losses by comparative genomic in situ hybridization. Hum. Genet. 90, 590–610, which is incorporated by reference as if fully set forth herein.

Since the spectrum of the mixture of two different dyes is different than the spectra of both individual dyes, combinatorial fluorescence strategies allow the achievement of a high spectral variety in a sample by using only a very small number of dyes. For example, in the case of a normal male metaphase, 24 different chromosomes can be labeled to fluoresce with 24 different spectra by using combinations of only five different dyes.

Numerous methods are available to label DNA probes for use in FISH assays, including indirect methods whereby a hapten such as biotin or digoxigenin is incorporated into DNA using enzymatic reactions. Following hybridization to a metaphase chromosome spread or interphase nucleus, a fluorescent label is attached to the hybrid through the use of immunological methods. More recently, fluorescent dyes have been directly incorporated into probes and detected without the use of an intermediate step. Standard FISH dyes include fluorescein. rhodamine, Texas-Red and cascade blue, and multiprobe FISH analysis can be accomplished by labeling different probes with different haptens or fluorescent dyes and combinations thereof, known in the art as combinatorial labeling [see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. Alternatively a pool of a given probe may be divided into sub-pools, each labeled with a different fluorophore, after which the sub-pools are regrouped to yield otherwise similar hybridization results, a method known in the art as combinatorial hybridization [see, du-Manoir et al. (1993) Detection of complete and partial chromosome gains and losses by comparative genomic in situ hybridization. Hum. Genet. 90, 590–610, which is incorporated by reference as if fully set forth herein]. According to both labeling strategies obtained are combinatorial probes. Thus, when any of the terms "combination of fluorophores" or "combinatorial fluorescent strategy" is used herein in this document and especially in the claims below, it refers both to combinatorial labeling and to combinatorial hybridization as described above.

The use of combinatorial fluorophores for chromosome painting and karyotyping, multicolor chromosome banding and comparative genome hybridization is described in details in U.S. patent application Ser. No. 08/635,820, filed Apr. 22, 1996, and in Science magazine [E. Schroeck et al. (1996) Multicolor spectral karyotyping of human chromosomes. Science, 273, 494–497], both are incorporated by reference as if fully set forth herein.

The main progress described in Science is that whole genome scanning by spectral imaging allows instantaneous visualization of defined emission spectra for each human chromosome after fluorescence in situ hybridization (FISH). By means of computer separation (classification) of spectra, spectrally-overlapping chromosome-specific DNA probes are resolved and all human chromosomes are simultaneously identified.

This spectral imaging approach combines Fourier spectroscopy, charge coupled device (CCD)-imaging, and optical microscopy to measure simultaneously at all points in the sample emission spectra in the visible and near-infrared spectral range. This allows the use of multiple spectrally overlapping probes. The approach is based on the measurement of a discrete spectrum (identified from a sequence of intensities at every pixel measured at many different wavelengths), which facilitates the discrimination of multiple fluorophores. In dramatic contrast to conventional epifluorescence microscopy in which fluorochrome discrimination is based on the measurement of a single intensity through a fluorochrome specific optical filter (narrow band filter) [see, Speicher et al. (1996) Nature Genetics. 12:368–375; and Speicher et al. (1996) Bioimaging 4:52–64], the use of spectral karyotyping allows all information within the spectrum of emitted light to be used for analysis.

The spectral-based method for discriminating spectrally overlapping fluorophores (classification) is readily extended to a large number of fluorochromes, provided there are measurable and consistent differences in the emission spectrum of each fluorochrome.

Simultaneous identification of each human chromosome in metaphase preparations, an approach referred to as spectral karyotyping, is also reported. To this end, chromosome-specific composite libraries generated by polymerase chain reaction (PCR) from flow-sorted human chromosomes are directly labeled with nucleotides conjugated to five different fluorophores or combinations thereof. A composite probe set containing all 24 chromosomes is then hybridized to metaphase chromosomes. Chromosome-specific labeling is achieved by suppression hybridization. Specifically, repetitive sequences in the composite libraries are blocked by the addition of an excess of unlabeled human Cot-1 DNA.

The hybridization is presented in both RGB display and classification colors. Display colors allow all human chromosomes to be readily visualized after spectral imaging, and based on spectral measurements at each pixel, a chromosome classification algorithm is applied to spectrally karyotype all human chromosomes. One of the most important analysis algorithms is the spectral-based classification algorithm that enables multiple different spectra in the image to be identified and highlighted in classification-colors. This allows assignment of a specific classification-color to all human chromosomes based on their spectra. This algorithm assumes that the (reference) spectrum of each chromosome has been measured and stored in a reference library in the Computer. A classification-color is assigned to each pixel in the image according to the classification-color assigned to the reference spectrum that is most similar to the spectrum at that given pixel. A minimal square error algorithm as shown in Equation 1:

$$S_{x,y,n} = \int_{\lambda 1}^{\lambda 2} (I_{x,y}(\lambda) - I_n(\lambda))^2 d\lambda \tag{1}$$

is computed for every pixel, in which $I_{x,y}(\lambda)$ is the normalized spectrum at pixel coordinates x,y and $I_n(\lambda)$ represents the normalized reference spectrum for each of the chromosome n=1, 2, . . . , 23, 24. After calculating the value of $S_{x,y,n}$ for all reference spectra, the smallest value is chosen and an artificial classification-color is assigned to that pixel in accordance with the classification-color assigned to the most similar reference spectrum.

The potential of spectral karyotyping as a screening method for chromosomal aberrations was further explored by analyzing clinical samples from multiple laboratories where conventional banding methods or FISH with chromosome painting probes had been previously performed. In all cases, G-banding and spectral karyotyping revealed consistent results. In some cases, Giemsa-banding was not sufficient to entirely interpret the chromosomal aberrations. In these cases, the diagnosis of chromosomal aberrations by spectral karyotyping was confirmed with conventional dual-color FISH analysis. The smallest discernible aberration analyzed for this report was a translocation t(1;11) (q44;p15.3) in which the reciprocal translocation was unrecognizable by conventional banding analysis. The origin of the chromosomal material that contributed to the reciprocal translocation was correctly classified. The translocated segments on chromosomes 1 and 11 had been confirmed by subtelomere specific cosmid probes for chromosomes 1q and 11p. On the basis of the location of the probes utilized, the size of the alteration was estimated to be >1,500 kbp. In a second case, banding analysis suggested a translocation of a segment of chromosome 4 to chromosome 12. Spectral karyotyping unambiguously identified and classified the origin of the additional chromosomal material as being derived from chromosome 4. To determine the limit of sensitivity of spectral karyotyping, a case with a submicroscopic translocation (unrecognizable in both metaphase and prometaphase chromosomes) involving chromosomes 16 and 17 was examined. This t(16;17) had been previously demonstrated by FISH with cosmid probes and the reciprocal interchange of chromatin estimated at approximately 500 kbp. Spectral karyotyping with metaphase chromosomes from this patient failed to identify the known t(16;17) suggesting that the limit of sensitivity for metaphase chromosome analysis with currently available painting probes to be between 500–1,500 kbp.

To demonstrate that spectral karyotyping is an approach that can be used to complement conventional banding analysis, hybridization on previously G-banded chromosomes was also performed. Probably due to the trypsin digestion that is required for G-banding, the signal intensity was slightly reduced as compared to metaphases that were not previously G-banded. The loss of signal intensity was approximately 10%, and could therefore easily be compensated for by prolonged exposure times. A slightly increased noise at the edges of previously G-banded chromosomes compared to non-banded chromosomes was also observed. However, the classification of the metaphase could be readily achieved.

Yet, the method disclosed in Science magazine and described above has limitations. A spectral image composed of 300×300 pixels and fifty wavelengths for each spectrum is a file of ca. 4.5 Megabytes. In the system described in Science the interferogram for each pixel contains at least double number of data, ca. 9.0 Megabytes for each measurement, before the Fourier Transform is calculated. This is a large amount of data, which takes a long time to collect and occupies a large amount of memory to store.

The epifluorescence microscopy in which fluorochrome discrimination is based on the excitation through a narrow excitation filter and measurement of the fluorescence emission through a fluorochrome specific optical filter (a second narrow band filter) as described by Speicher et al. (1996) Nature Genetics. 12:368–375; and Speicher et al. (1996) Bioimaging 4:52–64, is also applicable for chromosome classification, however, this method suffers inherent limitations as follows.

The filters employed for obtaining data are fluorochrome specific. Since the excitation and emission spectra of most fluorophores available for chromosome painting overlap to a large extent, these filters are selected both (i) very narrow (e.g., about 5–10 nm each) and, (ii) depending on the exact fluorophores employed and the degree to which their excitation and emission spectra overlap, the filters are in many cases selected to filter peripheral light (light from the shoulders and not from the peak of excitation or emission).

As such, these filters leave most of the data present in the examined samples filtered out or in other words, uncollected, resulting in a lower sensitivity and specificity of the final pixel classification. The loss of photons in this method is so large (because it occurs in both the excitation and the emission channels), that the signal may decrease by 2 orders of magnitude with respect to a measurement of unfiltered emission.

There is, however, one advantage associated with epifluorescence microscopy as compared with interferometric imaging. The epifluorescence microscopy, which employs a small number of filters, has the potential, if developed according to the present invention, to shorten the measurement time without losing signal to noise ratio, by requiring the collection of less frames than in the case of interferometric spectral imaging, which collects the full spectral information.

The present invention is directed at providing a method which enjoys both the advantage of filter based epifluorescence microscopy and the high signal to noise ratio of interferometric imaging.

SUMMARY OF THE INVENTION

According to the present invention there is provided a method and apparatus for classification of pixels into groups of pixels according to their spectra and for determining the amount of fluorophores present in a pixel.

According to further features in preferred embodiments of the invention described below, provided is a method of classification of pixels into groups of pixels according to their association with a single fluorophore or a combination of fluorophores selected from a plurality of fluorophores each of the fluorophores having characterizing emission spectrum and specifying emission peak, the method comprising the steps of (a) providing a plurality of wide-band emission filters; (b) for each of the pixels, recording emitted light intensity as retrieved after passing through each one of the plurality of emission filters, such that each of the pixels is representable by a vector of a plurality of dimensions, the number of dimensions being equal to the number of the wide-band emission filters; (c) using an algorithm for evaluating the presence of each of the plurality of fluorophores in each of the pixels, thereby classifying each of the pixels into a group of pixels according to its association with a single fluorophore or combination of fluorophores.

According to still further features in the described preferred embodiments provided is a method of classification of pixels into groups of pixels according to their association with a single fluorophore or a combination of fluorophores selected from a plurality of fluorophores, each of the fluorophores having characterizing excitation and emission spectra and specifying excitation and emission peaks, the method comprising the steps of (a) providing a plurality of pairs of wide-band excitation filters and wide-band emission filters; (b) exciting fluorophores of each of the pixels with light filtered through one of the wide-band excitation filters, and recording emitted light intensity as retrieved after passing through its paired emission filter; (c) repeating step (b) for all of the plurality of pairs of filters, such that each of the pixels is representable by a vector of a plurality of dimensions, the number of dimensions being equal to the number of the plurality of pairs of filters; (c) using an algorithm for evaluating the presence of each of the plurality of fluorophores in each of the pixels thereby classifying each of the pixels into a group of pixels according to its association with a single fluorophore or combination of fluorophores.

According to still further features in the described preferred embodiments provided is an apparatus for classification of pixels into groups of pixels according to their association with a single fluorophore or a combination of fluorophores selected from a plurality of fluorophores, each of the fluorophores having characterizing excitation and emission spectra and specifying excitation and emission peaks, the apparatus comprising (a) a light source; (b) a plurality of pairs of wide-band excitation filters and wide-band emission filters; (c) a control device for (i) selecting a pair of the plurality of pairs; (ii) exciting fluorophores of each of the pixels with light originating from the light source filtered through one of the vide-band excitation filters; and (ii) repeating steps (i)–(ii) for all of the plurality of pairs of filters, such that each of the pixels is representable by a vector of a plurality of dimensions, the number of dimensions being equal to the number of the plurality of pairs of filters; (c) a light intensity recording device for recording emitted light intensity as retrieved after passing through the emission filters; and (d) a computing device including an algorithm for evaluating the presence of each of the plurality of fluorophores in each of the pixels, thereby classifying each of the pixels into a group of pixels according to its association with a single fluorophore or combination of fluorophores.

According to still further features in the described preferred embodiments the computing device serves for giving pixels belonging to each of the groups of pixels a unique artificial color, such that pixels belonging to each of the groups are distinguishable from one another.

According to still further features in the described preferred embodiments at least two of the wide-band emission filters have overlapping bandpasses.

According to still further features in the described preferred embodiments at least two of the wide-band excitation filters have overlapping bandpasses.

According to still further features in the described preferred embodiments pixels belonging to each of the groups of pixels are given a unique artificial color, such that pixels belonging to each of the groups are distinguishable from one another.

According to still further features in the described preferred embodiments the algorithm is a linear decomposition algorithm.

According to still further features in the described preferred embodiments the fluorophores are bound to genetic material of metaphase chromosomes, such that genetic material of each of the metaphase chromosomes is bound to a different fluorophore or combination of fluorophores.

According to still further features in the described preferred embodiments the number of the plurality of fluorophores is five.

According to still further features in the described preferred embodiments the number of the plurality of pairs of filters is five.

According to still further features in the described preferred embodiments the number of the plurality of fluorophores equals the number of the plurality of pairs of filters.

According to still further features in the described preferred embodiments each of the wide-band emission filters is selected to have a bandpass corresponding to the emission spectrum of one fluorophore of the plurality of fluorophores on one hand, and to allow a high throughput of light emitted from the one fluorophore on the other hand.

According to still further features in the described preferred embodiments each of the wide-band excitation filters is selected to have a bandpass corresponding to the excitation spectrum of one fluorophore of the plurality of fluorophores on one hand, and to allow a high throughput of excitation light on the other hand.

According to still further features in the described preferred embodiments the bandpass of at least one of the wide-band emission filters is selected to overlap with the emission peak of its corresponding fluorophore.

According to still further features in the described preferred embodiments the bandpass of at least one of the wide-band excitation filters is selected to overlap with the excitation peak of its corresponding fluorophore.

According to still further features in the described preferred embodiments the wide-band emission filters are represented by a single tunable filter.

According to still further features in the described preferred embodiments the wide-band excitation filters are represented by a single tunable filter.

According to still further features in the described preferred embodiments the tunable filters are selected from the group consisting of AOTF and LCTF.

The above method and apparatus may also be employed for determining the amount (relative or absolute amount) of fluorophores in a pixel.

Thus, according to still further features in the described preferred embodiments provided is a method of determining the amount of a single fluorophore or a combination of fluorophores selected from a plurality of fluorophores associated with a pixel each of the fluorophores having characterizing emission spectrum and specifying emission peak, the method comprising the steps of (a) providing a plurality of wide-band emission filters; (b) recording emitted light intensity as retrieved after passing through each one of the plurality of emission filters, such that the pixel is representable by a vector of a plurality of dimensions, the number of dimensions being equal to the number of plurality of wide-band emission filters; (c) using an algorithm for evaluating the amount of each of the plurality of fluorophores in the pixel.

According to still further features in the described preferred embodiments provided is a method of determining the amount of a single fluorophore or a combination of fluorophores selected from a plurality of fluorophores associated with a pixel, each of the fluorophores having characterizing excitation and emission spectra and specifying excitation and emission peaks, the method comprising the steps of (a) providing a plurality of pairs of wide-band excitation filters and wide-band emission filters; (b) exciting fluorophores of the pixel with light filtered through one of the wide-band excitation filters, and recording emitted light intensity as retrieved after passing through its paired emission filter; (c) repeating step (b) for all of the plurality of pairs of filters, such that the pixel is representable by a vector of a plurality of dimensions, the number of dimensions being equal to the number of the plurality of pairs of filters; (c) using an algorithm for evaluating the amount of each of the plurality of fluorophores in the pixel.

According to still further features in the described preferred embodiments provided is an apparatus of determining the amount of a single fluorophore or a combination of fluorophores selected from a plurality of fluorophores associated with a pixel, each of the fluorophores having characterizing excitation and emission spectra and specifying excitation and emission peaks, the apparatus comprising (a) a light source, (b) a plurality of pairs of wide-band excitation filters and wide-band emission filters; (c) a control device for (i) selecting a pair of the plurality of pairs; (ii) exciting fluorophores of the pixel with light originating from the light source filtered through one of the wide-band excitation filters; and (iii) repeating steps (i)–(ii) for all of the plurality of pairs of filters, such that the pixel is representable by a vector of a plurality of dimensions, the number of dimensions being equal to the number of the plurality of pairs of filters; (c) a light intensity recording device for recording emitted light intensity as retrieved after passing through the emission filters; and (d) a computing device including an algorithm for evaluating the amount of each of the plurality of fluorophores in the pixel.

The present invention successfully addresses the shortcomings of the presently known configurations by providing a system for classification of pixels according to their spectra and determining the amount of fluorophores present in a pixel which takes into account both specificity and throughput, thereby the measurement results in optimal signal to noise ratio.

It is an object of the present invention to provide a method and system for analysis of chromosomes.

It is another object of the present invention to provide a method and system for quick detection of chromosomal aberrations.

It is yet another object of the present invention to provide a method and system for providing a color karyotype.

It is still another object of the present invention to provide a method and system which can accomplish the above objectives of the invention with high signal to noise ratio and in a short time, by employing wide band filters for data collection.

These and other objectives of the invention are further detailed below.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The invention herein described, by way of example only, with reference to the accompanying drawings, wherein.

DESCRIPTION OF THE PREFERRED EMBODIMENTS

Figure 1:
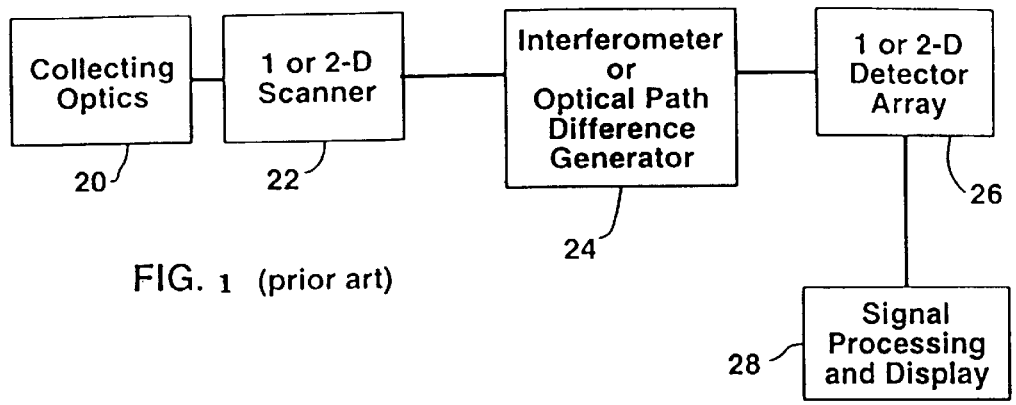
FIG. 1 is a block diagram illustrating the main components of an imaging spectrometer constructed in accordance with U.S. Pat. No. 5,539,517 (prior art)

The present invention is of a method and apparatus for classification of pixels into groups of pixels according to their fluorescence spectra, as filtered through a plurality of wide band excitation and/or emission filters and for determining the amount, either relative or absolute, of fluorophore(s) present in a pixel. The present invention can be used for classification of pixels presenting in situ fluorescently painted chromosomes into groups of pixels, each group is associated with genetic material derived from a different chromosome and for determining the amount of fluorophores present in any of the pixels. Specifically, the present invention can be used for chromosome classification, to provide color (spectral) karyotypes and thereby detect chromosomal aberrations.

The principles and operation of the method according to the present invention may be better understood with reference to the drawings and accompanying descriptions.

Spectral imaging is the technology that enables the measurement of the spectrum of light emitted by every point (pixel) of an object. A spectral imager (also referred herein as imaging spectrometer) is an instrument that measures and stores in memory for later retrieval and analysis the spectrum of light emitted by every point of the object which is placed in its field of view. A spectral image is a collection of spectra of the object measured by a spectral imager. It is usually organized as an intensity function defined in a three dimensional space in which two dimensions are of an image (x and y), and one is of a spectral axis ($\lambda$). As such, a spectral image is usually referred to as a "cube" of data or "spectral cube".

Prior art teaches different methods of measuring spectral images (i.e., spectral cubes). Devices designed according to these methods include light collection optics; a dispersion element (e.g., a grating), filter(s) (e.g., narrow interference filters, AOTF or LCTF) or an interferometer; focusing optics; and a two-dimensional array of detectors (typically a CCD in the visible range and other types of detectors in the infrared range).

Each method has advantages and disadvantages, however as shown in U.S. Pat. No. 5,539,517 and in Journal of Microscopy [Vol. 182, pp.133–140, 1996], both are incorporated by reference as if fully set forth herein, a spectral imager based on a special type of triangular interferometer has advantages of compactness and stability that more conventional spectral imagers do not have. A spectral imager in accordance with the invention disclosed in U.S. Pat. No. 5,539,517 was developed by Applied Spectral Imaging Ltd., Industrial Park, Migdal Haemek, Israel and is referred hereinbelow as SPECTRACUBE™.

The SPECTRACUBE™ system, which is described hereinbelow in more detail, served to obtain spectra of pixels presenting painted chromosomes, which spectra were thereafter used for classification according to the method of the present invention.

The importance of a spectral image measurement resides in the fact that the spectrum of light carries information about the composition of matter of which the object is made, and therefore it can be used to map and visualize phenomena which cannot be seen otherwise (e.g., by regular imaging either black and white or color). As a color image is the next step after a black and white image, a spectral image is the next step after a color image. Similarly to the difference of green hues between the leaves of two different types of trees or between a young leaf and an old one, two fluorescent dyes such as Texas Red and Rhodamine appear the same color to the human eye but they are well distinguished by a spectrograph with ten nanometers resolution. A complex biological system such as a white blood cell stained with Giemsa, looks to the eye through the microscope in transmission of white light, as an object with structures composed of regions of purple, blue and reddish colors in different levels of intensity. Since the colors as perceived by the human eye are composed of combinations of only three colors, red, green and blue (RGB), the number of different regions in the cell that can be classified by color is very limited. For each point of the same cell a spectral imager measures a spectrum which depends on the chemical materials present at that point, and this is a function of wavelength which contains the order of fifty to two hundred data (depending on the material and the spectral resolution of the measurement) instead of only three as for a color image. As a result, small spectral differences or shifts between pixels can be detected by a spectral imager, which the eye would recognize as belonging to the same color class, and therefore many more classes of biological structures or components can be distinguished in the cell using a spectral imager, as compared with the human eye or an equivalent (e.g., conventional RGB color image).

For example, in Fluorescence Imaging Spectroscopy and Microscopy, edited by X. F. Wang and B. Herman, Vol. 137 pp. 87–124, 1996, John Wiley & Sons, a nuclear wall is shown sharply distinct from the rest of the nucleus in a spectral image, contrary to a simple color image where the wall is perceived as part of the nucleus (see ibidem FIG. 4. 10d on page 115).

In E. Schroeck et al. (1996) Multicolor spectral karyotyping of human chromosomes. Science, 273, 494–497, it is shown how a spectral imager as disclosed in U.S. Pat. No. 5,539,517, is used in combination with fluorescence in situ hybridization (FISH) techniques to analyze combinatorially painted chromosomes (human and animals), so that karyotyping, chromosome number and chromosomal aberrations can be easily and reliably found and characterized.

According to this technique each chromosome is hybridized with complementary DNA material which contains a different combination of fluorescent dyes out of a larger set of dyes, such that each chromosome of a metaphase spread emits a different fluorescence spectrum uniformly over its surface. Typically, each chromosome is labeled with a different combination of up to three dyes (e.g., one, two or three dyes) selected from a set of five dyes, resulting in 24 different fluorescence spectra, one for each chromosome. This is done with human (requiring 24 different spectra or 24 combinations of dyes), mouse and monkey chromosomes (for which the number is different than 24), and with healthy and diseased (e.g., cancerous) cells. The detection and identification of translocations while using this method is immediate and reliable because the different spectrum of a translocation stands out clearly in the surrounding chromosome, whereas the information carried by the G-banding technique widely used today is much less obvious for this purpose.

A spectral image composed of 300×300 pixels and fifty wavelengths for each spectrum is a file of ca. 4.5 Megabytes. In the system described in U.S. Pat. No. 5,539,517 the interferogram for each pixel contains at least double number of data, ca. 9.0 Megabytes for each measurement, before the Fourier transform is calculated. This is a large amount of data, which takes a long time to collect and occupies a large amount of memory to store.

The epifluorescence microscopy in which fluorochrome discrimination is based on the measurement of a single intensity through a fluorochrome specific optical filter (narrow band filter) as described by Speicher et al. (1996) Nature Genetics. 12:368–375; and Speicher et al. (1996) Bioimaging 4:52–64, is also (applicable for chromosome classification, however, as described in the Background section above, this method suffers inherent limitations since the filters employed for obtaining data are fluorochrome specific. The emission spectra of most fluorophores available for chromosome painting overlap to a large extent, these filters are selected both (i) very narrow (e.g., about 5–10 nm each) and, (ii) depending on the exact fluorophores employed and the degree to which their emission spectra overlap, the filters are in many cases selected to filter peripheral light (light from the shoulders and not from the peak of emission). As such, these filters leave out most of the information present in the examined samples, resulting in lower signal to noise ratio and higher uncertainty for purposes of classification. This results in lower sensitivity and specificity of a diagnosis based on this analysis.

The following further addresses the limitations of the epifluorescence microscopy approach for classification as compared with the interferometric approach and highlights the advantages of the method according to the present invention.

In U.S. patent application Ser. Nos. 08/575,191; 08/635,820; 08718,831 and U.S. Pat. No. 5,719,024 methods and apparatuses for chromosome classification. Shared by these methods is the step of painting the chromosomes using whole chromosome paints. Thereafter, the analysis and apparatus employed divert according to the method of choice.

According to one method an interferometer based spectral imager is employed to collect a complete fluorescence spectra from each pixel of the analyzed sample, which is thereafter analyzed using a reference template.

According to another method a series of dedicated wide-band decorrelation matched filters (e.g., interference, AOTF, LCTF electronically driven with wide wavelength bands or others) designed on the basis of a decorrelation statistical analysis, such as principal component analysis (PCA), of the measured spectra are used to collect decorrelated spectral data from the analyzed sample.

These measurement apparatuses are all characterized by high signal to noise ratio because the photon rejection rate is very low: the interferometer method is not limited by narrow filters for wavelength separation, and the decorrelation matched filters (although not fully transmitting) transmit through the whole spectral range of the fluorescence emission. These methods are therefore referred to herein as "high photon throughput systems" or HPTS.

In Speicher et al. (1996) Nature Genetics. 12:368–375 and in Speicher et al. (1996) Bioimaging 4:52–64, a method for chromosome classification using a set of differentiating filters which are narrow in nature, which shall be referred to herein as "low photon throughput system" or LPTS. In the LPTS differentiating filters the excitation filters are narrow but chosen to transmit wavelengths where substantially only one dye at a time is excited, and similarly the corresponding emission filters are narrow and chosen in narrow wavelength ranges where only one dye at a time emits.

The LPTS concept could give a good dye separation (even at low signal to noise ratio) only if each dye used in the combinatorial painting could be excited and could be measured in wavelength ranges which do not overlap among themselves. Unfortunately, all existing and practically used dyes overlap to a large extent, both in the excitation and in the emission bands, and as a result the measured signals cannot be completely dye-specific. This phenomenon is further evident from FIG. 3.

Figure 3:
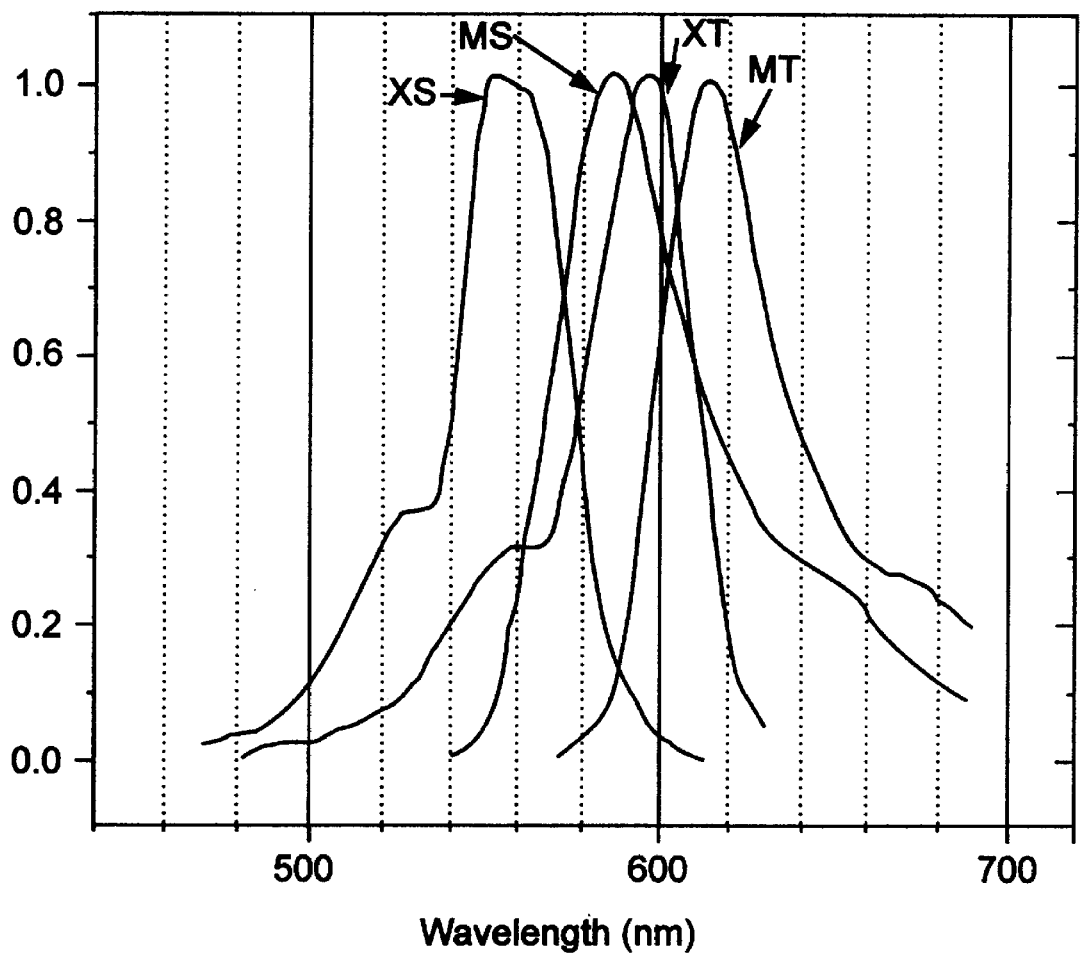
FIG. 3 illustrates the excitation and emission spectra of two fluorophores having overlapping excitation and emission spectra (such as the pairs TEXAS RED and SPECTRUM ORANGE or Cy5 and Cy5.5) and corresponding narrow differentiating excitation and emission filters used according to the principles of prior art low photon throughput system (LPTS) with these dyes.

FIG. 3 presents the excitation (X) and emission (M) spectra of first (T) and second (S) fluorophores having overlapping excitation and emission spectra, e.g., TEXAS RED and SPECTRUM ORANGE or Cy5 and Cy5.5. The corresponding narrow (10 nm in this case) excitation and emission filters (F) which would be used in a prior art LPTS with these dyes are shown as arrows. It can be seen that the resulting low signal to noise ratio is due to two factors: (i) high photon rejection ratio of the narrow filters, and (ii) the transmission wavelengths of the filters are far from the peaks of the excitation and emission spectra.

In order for the filters to be specific to each dye separately and avoid overlap as much as possible (which can never be avoided completely), they have to be very narrow, and the narrower the better. However, as a direct consequence both the number of photons incident on the sample in the excitation path and the number of photons which are eventually measured in the emission path are inherently small. As a result the signal to noise ratio of the measurement is very low, about two orders of magnitude lower than either unfiltered or HPTS measurement according to preferred embodiments of the present invention.

According to the present invention wide band excitation and emission filters are employed for classification and the inherent high photon throughput of such filters results in a higher signal to noise ratio, higher reliability of the measurement and as a consequence a higher sensitivity and specificity ol the resulting diagnosis.

As further detailed in the Examples section below, the spectral overlap in both the excitation and emission spectra of the fluorescent dyes employed is taken into account under certain assumptions of linearity of the signals by dedicated linear decomposition mathematical algorithms.

Briefly, the following points are noted:

First, according to the present invention, as compared with the prior art LPTS, the lower-specificity of the signals due to the larger width of the excitation and emission filters, is compensated for by higher signal to noise ratio and by a linear decomposition algorithm.

Second, although the example shown below refers to combinatorial labeling and classification of human chromosomes, it is easily recognized by one ordinarily skilled in the art that the present invention applies to any type of sample which contains multiple regions stained or labeled with different fluorophores or combinations thereof.

Thus, the present invention is directed at providing a method which enjoys both the potentially short measurement time of a small number of frames taken through a small number of filters in conjunction with epifluorescence microscopy and the high signal to noise ratio capability of interferometric spectral imaging, using wide band filters for data collection.

According to the present invention provided is a method of classification of pixels into groups of pixels according to their association with a single fluorophore or a combination of fluorophores (e.g., two, three or four different fluorophores). The fluorophores are selected from a plurality of fluorophores (e.g., four or more different fluorophores). Being different, each of the fluorophores has characterizing excitation and emission spectra and specifying excitation and emission peak(s), see, for example, FIG. 4b.

According to one embodiment of the method according to the present invention advantage is taken of the characterizing emission spectra and peaks of the fluorophores. To this end provided are a plurality of wide-band emission filters, which are sequentially used to collect data from each of the pixels to be classified. Thus, for each of the pixels, emitted light intensity as retrieved after passing through each one (at a time) of the plurality of emission filters is recorded. As a result, each of the pixels is representable by a vector of a plurality of dimensions, the number of dimensions being equal to the number of the wide-band emission filters employed. Thereafter a suitable algorithm is employed for evaluating the presence of each of the plurality of fluorophores in each of the pixels. Thereby each of the pixels is classified into a group of pixels according to its association with a single fluorophore or any given combination of fluorophores.

According to another and presently preferred embodiment of the method according to the present invention advantage is taken of both the characterizing emission and excitation spectra and peaks of the fluorophores. To this end provided are a plurality of pairs of wide-band excitation filters and wide-band emission filters, which are sequentially used as pairs to collect data from each of the pixels to be classified. Thus, fluorophores of each of the pixels are excited with light filtered through one of the wide-band excitation filters, and emitted light intensity as retrieved after passing through its paired emission filter is recorded. This procedure is repeated for all pairs of filters, such that each of the pixels is representable by a vector of a plurality of dimensions, the number of dimensions being equal to the number of filter pairs. As before, eventually a suitable algorithm is used for evaluating the presence of each of the plurality of fluorophores in each of the pixels. As a result, each of the pixels is classified into a group of pixels according to its association with a single fluorophore or any combination of fluorophores.

According to another embodiment of the invention provided are a plurality of wide band excitation and emission filter pairs, with no requirement on their transmission spectrum other than to be wide (e.g., in the order of tenth the width of the spectral range, e.g., 20–70 nm, preferably 30–50 nm) which are sequentially used as pairs to collect data from each of the pixels to be classified.

Thus, fluorophores of each of the pixels are excited with light filtered through one of the wide-band excitation filters, and emitted light intensity as retrieved after passing through its paired emission filter is recorded. This procedure is repeated for all pairs of filters, such that each of the pixels is represented by a vector of a plurality of dimensions. The number of dimensions being equal to the number of filter pairs. As before, eventually a suitable algorithm is used for evaluating the presence of each of the plurality of fluorophores in each of the pixels. As a result, each of the pixels is classified into a group of pixels according to its association with a single fluorophore or any combination of fluorophores.

There are many aspects in which the wide-band filters employed according to the method of the present invention differ from the filters employed in the prior art method described in Speicher et al. (1996) Nature Genetics. 12:368–375; and Speicher et al. (1996) Bioimaging 4:52–64. Before turning to the description of the physical nature of the filters, a brief discussion of the considerations set forth while selecting the filters will be given. Thus, two main considerations are employed—throughput and dye specificity (throughput being more important since lack of dye specificity can be compensated for by the algorithms described below).

If selected independently both dye specificity and throughput are to be selected maximal, since maximal specificity and alternatively maximal throughput each independently results in higher signal to noise ratio. However, since throughput and dye specificity are competing parameters, the best one can do is to optimize them.

High specificity calls for narrow-band filters. Thus when dye specificity is the sole consideration, each of the excitation filters is selected substantially specific for exciting a specific fluorophore and each of the emission filters is selected substantially specific for transmitting light emitted by a specific fluorophore. On the other hand, when throughput is the sole consideration both excitation and emission filters are selected very wide such that throughput is maximized. However, dye specificity and throughput do not stand as sole independent considerations. Compensations must be made in both specificity and throughput such that the final result would have a maximal signal to noise ratio. Therefore, according to the present invention the band widths of both the excitation and emission filters are preferably selected as the optimum compensation most suitable for the fluorophores of choice. Some optimization could probably be obtained also with the spectral dependence of the filters' transmission. For example, high throughput is typically achieved under the central third of the excitation or emission spectra of any specific fluorophore since such spectra typically peaks at the central third region. Specificity on the other hand is achieved in regions which either completely do not overlap, or overlap to a minor extent (e.g., at a wavelength range wherein one fluorophore emits very strongly, whereas the other emits weakly). According to the present invention, led by these conflicting considerations one selects the most appropriate excitation and emission filters. Most suitable filters have a wide bandpass ranging between ca. 30 and 70 or more nm (see Table 4 below). The bandpass width selected for any of the wide-band filters depend to a great extent on the fluorophores of choice, and more particularly, on the degree the excitation or emission spectra of the selected fluorophores overlap.

The sole consideration taken into account in the prior art method described in Speicher et al. (1996) Nature Genetics. 12:368–375; and Speicher et al. (1996) Bioimaging 4:52–64, was specificity. Throughput received merely a secondary consideration, only where applicable without limiting specificity. As such, the filters employed thereat, both the excitation and emission filters, were selected highly narrow (e.g., about 10 nm), not overlapping filters which are typically positioned along the spectrum to cover parts of the shoulders (extreme thirds) of the excitation or emission spectra of the fluorophores employed therein.

Thus, according to a preferred embodiment of the present invention at least two, preferably more, say three, four or more, of the wide-band emission filters have overlapping bandpasses. Similarly, according to another preferred embodiment of the invention at least two, preferably more, say three, four or more, of the wide-band excitation filters have overlapping bandpasses. Thus, two or more of the filters (excitation or emission) excite or pass emitted light of two or more of the fluorophores.

Preferably each of the wide-band emission alters is selected to have a bandpass corresponding to the emission spectrum of one fluorophore of the plurality of fluorophores on one hand, and to allow a high throughput of light emitted from that fluorophore on the other hand. Preferably, the bandpass of at least one (preferably more than one, say two, three or four, etc.) of the wide-band emission filters is selected to overlap with the emission peak of its corresponding fluorophore.

Similarly, each of the wide-band excitation filters is selected to have a bandpass corresponding to the excitation spectrum of one fluorophore of the plurality of fluorophores on one hand, and to allow a high throughput of excitation light on the other hand. Preferably the bandpass of at least one (preferably more than one, say two, three or four, etc.) of the wide-band excitation filters is selected to overlap with the excitation peak of its corresponding fluorophore.

As further detailed below, a preferred algorithm according to the present invention is a linear decomposition algorithm. Such algorithm works in the following way. First, it assumes that the fluorescence spectra of different molecules add up, so that the spectrum of a pixel is the sum total of the spectra of all the molecules present in it. Second, it assumes that the spectra of the n fluorescence dyes chosen for the hybridization are independent from each other, meaning that none of them can be obtained as a linear combination of any of the others. Third, it mathematically expresses the signal from a pixel measured through each of the n pairs of excitation/emission filter as the sum of the signals obtained from each of the n dyes as measured through the same filters and weighted with the relative number of molecules (the n unknowns) present in the pixel of that particular dye, thereby building a set of n linear equations in n unknowns. Fourth, it solves the n linear equations in n unknowns for every pixel, thereby finding the relative amount of each dye present in every pixel. Fifth, it uses the known painting scheme for each chromosome (meaning the combination of dyes with which each chromosome has been hybridized) to assign a chromosome number to each pixel. And sixth, it displays each pixel with an artificial color according to the chromosome number assigned to it such that pixels which belong to each of the groups are distinguishable from one another.

In a preferred embodiment and as further exemplified in the Examples section that follows the method herein described serves for metaphase chromosome classification and for the detection of chromosomal abnormalities. To this end, the fluorophores are bound (by hybridization) to genetic material of metaphase chromosomes, such that genetic material of each of the metaphase chromosomes is bound to a different fluorophore or combination of fluorophores. Thereby, when artificial colors are applied to groups of pixels as described, genetic material of each of the chromosomes is attributed a different color distinguished from the others.

In a preferred embodiment of the invention the number of emission filters and/or excitation filters, depending on the application, equal the number of fluorophores employed. However, this is not necessarily the case since less or more filters may be employed, yielding vectors which may still be analyzed by suitable decomposition algorithms or others.

According to one embodiment of the invention the wide-band excitation and/or emission filters are represented by a single tunable filter. The tunable filter is preferably either AOTF or LCTF. Providing the tunable filter with a set of information such that the filter is successively tuned to represent the wide band filters enjoy the advantage of no moving parts.

In accordance to the above described method, further according to the present invention provided is an apparatus to implement the method. Thus, the apparatus is for classification of pixels into groups of pixels according to their association with a single fluorophore or a combination of fluorophores selected from a plurality of fluorophores. Each of the fluorophores has characterizing excitation and emission spectra and specifying excitation and emission peaks. The apparatus includes a light source which provides a light beam which includes light in the wavelengths range suitable to excite the fluorophores of choice. The apparatus further includes a plurality of pairs of wide-band excitation filters and wide-band emission filters. The filters enjoy the above described features. The apparatus further includes an automatic, manual or semimanual control device (such as a computer). The control device serves for selecting a pair of the plurality of pairs, for exciting fluorophores of each of the pixels with light originating from the light source filtered through one of the wide-band excitation filters, and for repeating the above procedure for all of the filter pairs. The apparatus further includes a light intensity recording device which serves for recording emitted light intensity as retrieved after passing through the emission alters. As a result each of the pixels is representable by a vector of a plurality of dimensions, the number of dimensions being equal to the number of the plurality of pairs of filters. The apparatus further includes a computing device including an algorithm for evaluating the presence of each of the plurality of fluorophores in each of the pixels. Thereby, the computing device serves for classifying each of the pixels into a group of pixels according to its association with a single fluorophore or any of the combinations of fluorophores. In a preferred embodiment the computing device serves for giving pixels belonging to each of the groups of pixels a unique artificial color, such that pixels belonging to each of the groups are distinguishable from one another.

The method and apparatus according to the present invention is based on a small number of filters and high throughput, and therefore it needs only the collection of a small number of frames which results in a short measurement time as compared with the prior art interferometric based system [E. Schroeck et al. (1996) Multicolor spectral karyotyping of human chromosomes. Science, 273, 494–497], which requires the collection of many CCD frames for high spectral resolution and longer measurement time, yet provide a higher throughput as compared with another filter based prior art system [Speicher et al. (1996) Nature Genetics. 12:368–375; and Speicher et al. (1996) Bioimaging 4:52–64].

It will be appreciated by one ordinarily skilled in the art that employing similar method steps and apparatus components may be further used to determine the amount, either relative or absolute, of fluorophores present in a pixel of an examined specimen. This have advantages in many fields in biological research and diagnostics.

Reference is now made to the following examples, which together with the above descriptions, illustrate the invention in a non limiting fashion.

EXAMPLE 1

Chromosome Preparation for Measurement

The emergence of multicolor FISH has broadened the applications of molecular cytogenetics in basic research and genetic diagnosis. All existing multicolor FISH techniques require the use of fluorescent probes whose emission spectra can be separated with optical filters [Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls (University Heidelberg, both are incorporated by reference as if fully set forth herein].

A novel approach for FISH, employing the SPECTRACUBE™ system to measure and analyze multiple spectrally overlapping labeled probes (single and combinatorial), to classify chromosomes and therefore to detect chromosomal aberrations was recently introduced [E. Schroeck et al. (1996) Multicolor spectral karyotyping of human chromosomes. Science, 273, 494–497].

According to this novel approach, spectral bio-imaging which is a combination of Fourier spectroscopy, CCD-imaging and optical microscopy enabling the measurement of accurate spectral data simultaneously at all points of a biological sample, is used to visualize hybridization based multicolor appearance of all (i.e., 24) types of human chromosomes and to generate a color map of the human karyotype.

It will be appreciated by one ordinarily skilled in the art that many different sets of fluorophores and combinations thereof can be used to specifically label each of the 24 chromosomes of human or each chromosome of any other animal species. In this example a set of five dyes from which combinations of up to four dyes are used to differently label each of the 24 human chromosomes is used. However, the use of these dyes or combinations is for illustrative purpose only, and there is no intention to limit the scope of the invention to use of any specific dyes and/or combinations thereof.

Following is a description of the dyes and their combinations which are presently preferred.

Thus, 24 chromosome paints (1 through 22, X and Y, Table 1), each labeled with a different combination of four or less different fluorophores selected from a set of five fluorophores according to the combinatorial hybridization approach (a through e, Table 1), (see Table 1 for the different fluorophores and their spectral characteristics and Table 2 for the assignment of the fluorophores listed in Table 1 to obtain the 24 chromosome paints), were simultaneously hybridized with human mitotic chromosome spreads of few non-related male white blood cells, prepared for hybridization essentially as described in Ried et al. [Ried et al., (1992) Simultaneous visualization of seven different DNA probes by in situ hybridization using combinatorial fluorescence and digital imaging microscopy. Proc. Natl. Acad. Sci. USA 89, 1388–1392].

Hybridized chromosomes were viewed through an inverted fluorescence microscope connected to the SPECTRACUBE™ System and the emission spectrum of each pixel was measured.

It is clear to one ordinarily skilled in the art that other fluorophores, other combinations of fluorophores and different labeling approaches (e.g., combinatorial labeling) can be similarly used. Thus the body of information listed hereinbelow in Tables 1 and 2 is of an illustrative nature only, and there is no intention to limit the scope of the invention to the listed fluorophores, combinations of fluorophores and/or labeling technique.

TABLE 1

| Fluorophore | Symbol |
|---|---|
| Spectrum Orange | a |
| Texas-Red | b |
| Cy5 ™[1] | c |
| Spectrum Green | d |
| Cy5.5 ™[1] | e |

[1]from Amersham

TABLE 2

| Chromosome | Chromosome paint | Fluorophores |
|---|---|---|
| human chromosome 1 | 1 | b, c, d |
| human chromosome 2 | 2 | e |
| human chromosome 3 | 3 | a, c, d, e |
| human chromosome 4 | 4 | c, d |
| human chromosome 5 | 5 | a, b, d, e |
| human chromosome 6 | 6 | b, c, d, e |
| human chromosome 7 | 7 | b, c |
| human chromosome 8 | 8 | d |
| human chromosome 9 | 9 | a, d, e |
| human chromosome 10 | 10 | c, e |
| human chromosome 11 | 11 | a, c, d |
| human chromosome 12 | 12 | b, e |
| human chromosome 13 | 13 | a, d |
| human chromosome 14 | 14 | b |
| human chromosome 15 | 15 | a, b, c |
| human chromosome 16 | 16 | b, d |
| human chromosome 17 | 17 | c |
| human chromosome 18 | 18 | a, b, d |
| human chromosome 19 | 19 | a, c |
| human chromosome 20 | 20 | a |
| human chromosome 21 | 21 | d, e |
| human chromosome 22 | 22 | a, b, c, e |
| human chromosome X | X | a, e |
| human chromosome Y | Y | c, d, e |

EXAMPLE 2

The Apparatus Used to Retrieve Pixels Associated Spectra

FIG. 1 is a block diagram illustrating the main components of a prior art imaging spectrometer disclosed in U.S.

Pat. No. 5,539,517, which is incorporated by reference as if fully set forth herein. This imaging spectrometer has a high spectral (ca. 4–14 nm depending on wavelength) and spatial (ca. 30/M $\mu$m where M is the effective microscope or fore optics magnification) resolutions.

Thus, the prior art imaging spectrometer of FIG. 1 includes: a collection optical system, generally designated 20; a one-dimensional scanner, as indicated by block 22; an optical path difference (OPD) generator or interferometer, as indicated by block 24; a one-dimensional or preferably a two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, such as the four-mirror plus beamsplitter interferometer as further described in U.S. Pat. No. 5,539,517 (see FIG. 14 there).

Figure 2:
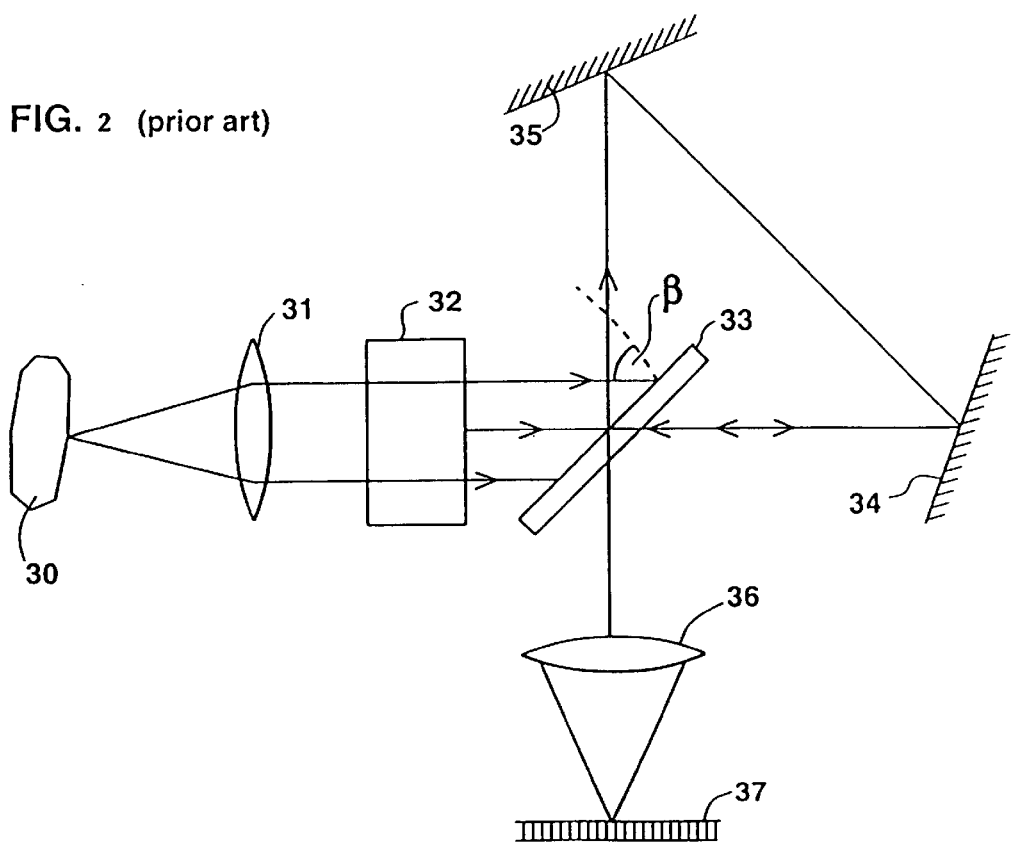
FIG. 2 illustrates a Sagnac interferometer, as used in an imaging spectrometer in accordance with U.S. Pat. No. 5,539,517 (prior art)

FIG. 2 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 2 the ray which is incident on the beamsplitter at an angle $\beta$ ($\beta=45°$ in FIG. 2) goes through the interferometer with an OPD=0, whereas a ray which is incident at a general angle $\beta-\theta$ undergoes an OPD given by Equation 2:

$$OPD(\beta,\theta,t,n)=t[(n^2-\sin^2(\beta+\theta))^{0.5}-(n^2-\sin^2(\beta-\theta))^{0.5}+2\sin\beta\sin\theta] \quad (2)$$

where $\beta$ is the angle of incidence of the ray on the beamsplitter; $\theta$ is the angular distance of a ray from the optical axis or interferometer rotation angle with respect to the central position; t is the thickness of the beamsplitter; and n is the index of refraction of the beamsplitter.

It follows from Equation 2 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convoluting the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

As mentioned above, an imaging spectrometer in accordance with the invention disclosed in U.S. Pat. No. 5,539,517 was developed by Applied Spectral Imaging Ltd., Industrial Park, Migdal Haemek, Israel and is referred herein as SPECTRACUBE™.

The SPECTRACUBE™ system optically connected to a fluorescent microscope was used to collect spectral data from painted chromosome samples, which data is herein analyzed in accordance with the method of the present invention, thereby, demonstrating the applicability and operability of the method. The specific spectral imager employed is the SPECTRACUBE™ system which has the characteristics listed hereinbelow in Table 3:

TABLE 3

| Character | Performance |
|---|---|
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

Thus, the prior art SPECTRACUBE™ system was used to acquire spectral data of every pixel of metaphase in situ painted chromosomes as described above. This data served to test the operability of the method according to the present invention by simulating emission filters as described below.

EXAMPLE 3

Simulation of the Method of the Present Invention Using Mathematical Wide-Band Filters for Chromosome Classification In combinatorial painting the genetic material of each chromosome is hybridized with complementary DNA strands labeled with a single fluorophore or a combination of fluorophores specific to that particular chromosome. In order to detect and identify the 24 different chromosomes of the human genome, a scheme (see Example 1 above) has been developed in which the combinations are from one to four out of five specially selected fluorophores. It is, however, evident that in principle other similar schemes can be used.

As a consequence, a pixel of a metaphase emits a fluorescence spectrum which depends on whether that pixel is associated with the background (any region between chromosomes), or with genetic material of any specific chromosome. In the background the theoretical signal should be zero. However, in practice, due to scattering from the metaphase chromosomes and further due to residual nucleic acid material, a low signal is measured also from the background.

A linear assumption is taken herein to enact pixel classification. According to the linear assumption the spectrum of each pixel is the sum of the fluorescence spectra of all fluorophores present in that pixel.

The fluorescence signal $R_i^j$ of a pixel in a chromosome or in a region of the sample dyed with a single fluorophore "i", as measured through the excitation and emission filters associated with fluorophore "j", is given by Equation 3:

$$F_i^j = N_i \int_\mu \int_\lambda S_j(\mu) Q_i(\lambda,\mu) O_j(\lambda) d\lambda d\mu = N_i a_{i,j} \quad (3)$$

Where $N_i$ is the number of fluorescent molecules present in a pixel of a chromosome painted only with dye number i, $\mu$ and $\lambda$ are the wavelength domains of the excitation and emission, respectively, $S_j$ is the excitation spectrum of dye number "j": this spectrum includes the contributions of the spectrum of the source itself and the spectral transmission of the excitation filter matched to "j", $O_j$ is the product of the spectral transmission of the microscope, of the emission filter for fluorophore "j", of the spectral response of the CCD detector and of any other optics on the emission path, $Q_i(\lambda, \mu)$ is the quantum efficiency of fluorophore i at wavelength $\lambda$ due to the excitation intensity at wavelength $\mu$. The function $Q_i(\lambda,\mu)$ is usually thought of as the product of two separate functions: an excitation spectrum $Q_i^x(\mu)$ and an emission spectrum $Q_i^e(\lambda)$, where $\lambda$ and $\mu$ vary in their respective range.

It should be noted that no assumptions concerning the spectral width and wavelength dependence of transmission of any of the filters and/or concerning the amount of overlap between the signals of the different dyes used in the combinatorial painting were made.

An expression analogous to Equation 3 can be written in general for any pixel belonging to a chromosome or sample region painted with n dyes, and the total fluorescence spectrum $F_p$ measured in that pixel through the excitation and emission filters matched to dye number "j" can then be written, under the linear assumption, as the sum of all the contributions of all the dyes present, each weighted by $n_i/N_i$, the relative number of molecules present of each dye in the pixel in question. For a pixel p on a chromosome painted with more than one dye from 1 to n, the signal $F_p^j$ measured through the excitation-emission filter pair "j" is written as follows (Equation 4):

$$F_p^j = \sum_{i=1}^n \frac{n_i}{N_i} F_i^j \quad (4)$$

where n is the number of dyes used in the labeling (n equals 5 in the present example) and the expression $R_i^j$ is taken from Equation 3 above.

Thus, if the chromosomes which are painted with only one dye are known in the metaphase, then the signals $R_i^j$ of these chromosomes are the known coefficients of the linear set of equations expressed by Equation 4. $F_p^j$ are known from the measurement, therefore in this set $n_i/N_i$ are the unknowns. If the set of coefficients $R_i^j$ are independent, then the set of linear equations of Equation 4 can be solved for $n_i/N_i$.

In a different embodiment the reference spectra $R_i^j$ are known from previous measurements and stored in a computer library. For example, this can be achieved by a set of measurements in which only single chromosomes are hybridized at a time with only one dye. In this case better results are obtained because non-specific hybridization of unwanted chromosomes is avoided in the reference spectra.

In the ideal case, the parameters $n_i$ and $N_i$ (i=1, ... n) are constant in each part of chromosome which is uniformly painted. In practice, their value changes somewhat from pixel to pixel because of biologic variability, measurement noise and other uncontrollable factors. For simplicity of the following description assume that they are constant. As such, deviations from uniformity are treated as noise in the measurement.

Furthermore, it was already pointed out that ideally, in a pixel of a chromosome painted with a single dye, let's say dye number i, $N_i$ is non zero, while $N_j=0$ for j≠i. In a pixel of a chromosome, painted with a combination of two dyes, say k and m, $n_k$ and $n_m$ are different than zero while all the other coefficients are ideally zero. A similar situation exists for combinations of three or four dyes. This is the basis for the classification of pixels into groups of pixels according to the present invention.

After solving the linear set of equations represented by Equation 4 above for a certain pixel, the ratios $n_i/N_i$ obtained for the various dyes are examined, and since the painting scheme for any of the chromosomes is known, the pixel is classified as belonging to one or the other chromosome depending on which combinations of $n_j/N_i$ are non zero. The set of ratios $n_j/N_i$ is therefore the pixel's classifier.

Of course, in practice the coefficients which should theoretically be zero are not exactly zero because of noise in the measurement, biological variability, scattering from nearby chromosomes, background emission, nonspecific hybridization, etc. These disturbances are unavoidable and should be treated separately in each specific application.

In the case of metaphase analysis, for example, a certain prior knowledge on the shape of chromosomal abnormalities such as translocations and insertions as sought by the method and apparatus according to the present invention, is enough to eliminate most noise related ambiguities. For example, all such features cross the chromosome perpendicularly to its longitudinal axis. As a result, a chromosomal feature which is classified differently than its surrounding region but does not fulfill this criterion, can be discarded as a chromosomal abnormality, and attributed to measurement noise.

In the case of chromosome classification, the first step is to hybridize and label the analyzed metaphase with a known dye combination scheme as for example described under example 1 above.

The second step is to image and record the metaphase or the sample by a digital video camera through each of the filter pairs (one for excitation and one for emission) in succession. The filters are designed and manufactured with a spectral transmission curve or profile to match the characteristics of each dye. Therefore one measurement consists of a stack of n images, one for each dye used and the data for each pixel is a vector of dimension n.

The third step is to analyze the data and classify each pixel of the image to a chromosome or background. The signals from the chromosomes which are painted with a single dye or the previously stored single dye spectra are the coefficients $R_i^j$ of the set of equations represented by Equation 4 above, because for the chromosome dyed with "i", $n_j/N_i=1$, and is equal to zero otherwise.

Alternatively, in order to decrease the effect of non specific staining in the definition of the reference data, the single dye chromosomes can be hybridized and measured separately. Thereafter, their respective n-vectors can also be used as reference vectors in Equation 4 with the same coefficients: this method gives better results.

Thus, according to the present invention, for each pixel, p, n signals are recorded, one for each set of filters, and its n dimensional vector is determined. Since there are n elements in the sum of Equation 4, for each pixel obtained is a set of n equations in n unknowns, the ratios $n_j/N_i$ (i=1, ... n) These equations can be solved and the ratios $n_j/N_i$ can then be found.

Each pixel can now be identified, because the set of ratios $n_j/N_i$ are known from the labeling scheme of each chromosome. Thus, a chromosome painted with a single dye has the corresponding ratio $n_j/N_i$ equal 1 and the others equal zero. A chromosome painted with a combination of two dyes has two of the ratios approximately equal to one half and the others equal zero. A chromosome painted with a combination of three dyes has three of the ratios approximately equal to a third and the others equal zero, etc.

Knowing the labeling scheme one can establish to which chromosome a pixel belongs to from the values of the ratios obtained for that pixel. Thereby each of the pixels can be assigned to represent genetic material of any specific chromosome.

The following is a summary of the assumptions made while implementing the method of the present invention: (i) linearity of the signals; (ii) uniformity of painting in each chromosome; (iii) a priori knowledge of the spectrum of the chromosomes painted with only one dye; (iv) knowledge of the painting combination scheme for all the chromosomes; and (v) independence of the equations of the set of Equation 4. In any other application of the method according to the present invention, all the assumptions above hold, except that (ii) and (iv) refer not to chromosomes, but to regions of pixels to be classified.

Following is an example of chromosome classification obtained simulating the method according to the present invention.

The example is given as a simulation based on spectral data obtained from a spectral cube of a combinatorially hybridized and labeled metaphase measured with the SD 200 model Spectral Imager manufactured by Applied Spectral Imaging Ltd. Migdal Haemek, Israel (see Example 2 above for the description and operation of the spectral imager employed).

The spectral cube contains complete fluorescence spectra in the range 470 to 800 nm. The measurement of these spectra as would have been obtained using vide-band emission filters according to the present invention is hereinbelow simulated by mathematical or algorithmic filters. These filters therefore represent emission filters, whereas the use of excitation filters is not simulated.

In the present example the mathematical filters were selected as square windows with which the emitted spectra are convoluted, so that the measurement of each pixel through a filter is simply simulated as an integral of the pixel's spectrum in the filter's range of transmission. Type of mathematical filter is equivalent to a wide bandpass filter with constant transmission which equals 100% in its band, and equals zero outside its band. In practice it is possible to obtain such filters from commercial manufacturers, and it will be obvious to one skilled in the art that the exact spectral shape of the filters (square or not) is not at all important for the operability of the present invention.

Figure 4A:
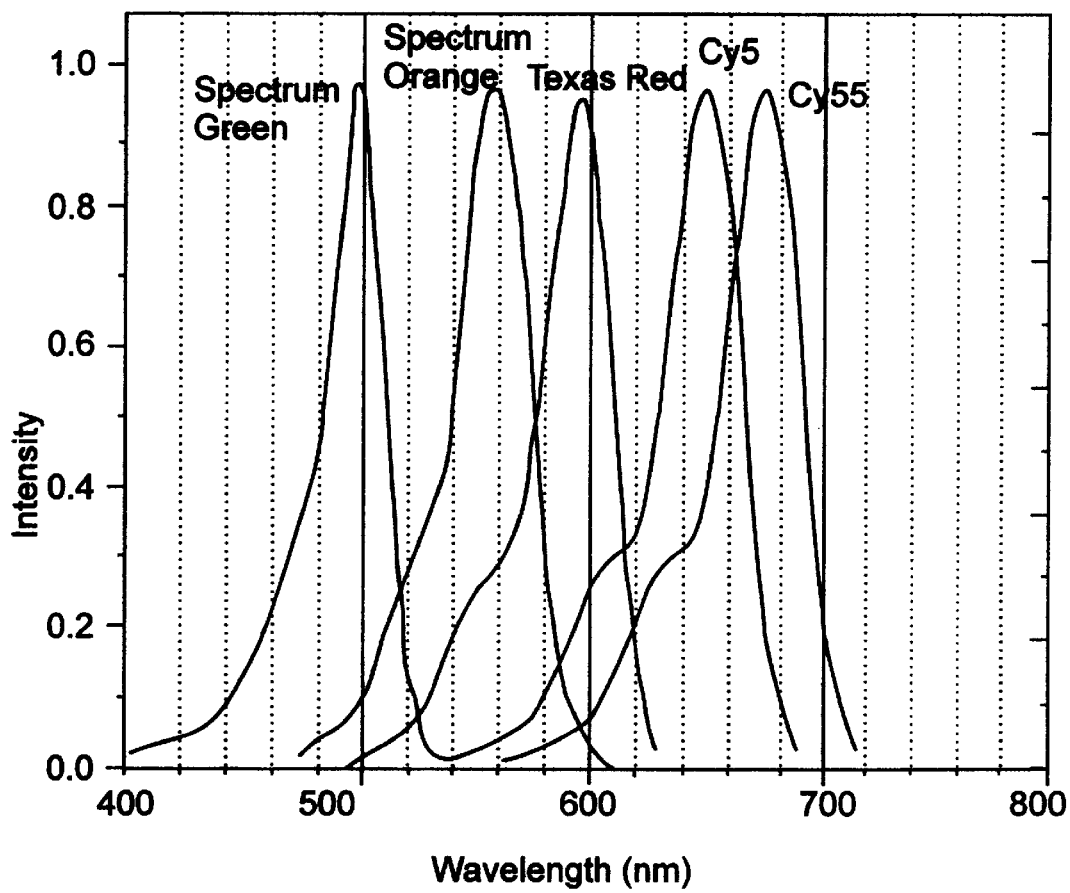
FIG. 4a illustrates the excitation spectra of the fluorophores (SPECTRUM (GREEN, SPECTRUM ORANGE, Texas Red, Cy5 and Cy5.5) employed to demonstrate the present invention and preferred excitation filters corresponding to these fluorophores.
Figure 4A:
Figure 4B:
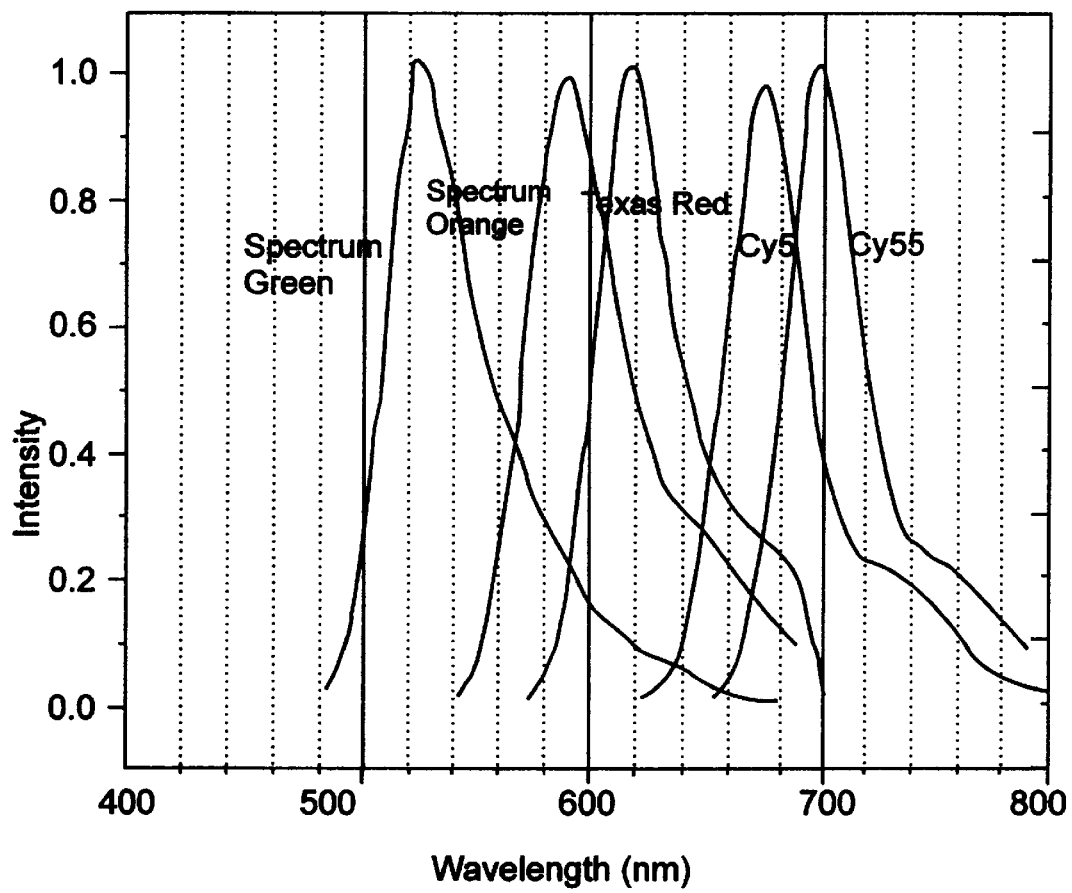
FIG. 4b illustrates the emission spectra of the fluorophores (SPECTRUM GREEN, SPECTRUM ORANGE, Texas Red, Cy5 and Cy5.5) employed to demonstrate the present invention and preferred emission filters corresponding to these fluorophores.

FIGS. 4a–b show the excitation and emission spectra of the five dyes (SPECTRUM GREEN, SPECTRUM ORANGE, Texas Red, Cy5 and Cy5.5) used in this example. The exact filter ranges should be experimentally optimized for best results. In our simulation they were chosen to be approximately centered with the corresponding spectra and capture 50–80% of the photons. One of the convenient advantages of the present invention is that in principle the results are not sensitive to the exact spectral shape of the filters, thereby simplifying their manufacture.

Table 4 provides an example of wide band excitation and emission filters that can be used to implement the method of the present invention. The ranges of these filters are also shown in FIGS. 4a and 4b along with the excitation and emission spectra of the dyes employed. The emission filters listed in Table 4 were used in the simulation of the method of the present invention.

TABLE 4

| Dye | Excitation Filter*, nm (band width) | Emission Filter, nm (band width) |
|---|---|---|
| SPECTRUM GREEN | 470–500 (30) | 520–580 (60) |
| SPECTRUM ORANGE | 520–570 (50) | 580–640 (60) |
| Texas Red | 560–600 (40) | 610–660 (50) |
| Cy5 | 620–655 (35) | 670–740 (70) |
| Cy5.5 | 640–680 (40) | 690–760 (70) |

*Excitation filters were not employed in the simulation.

Figure 5A:
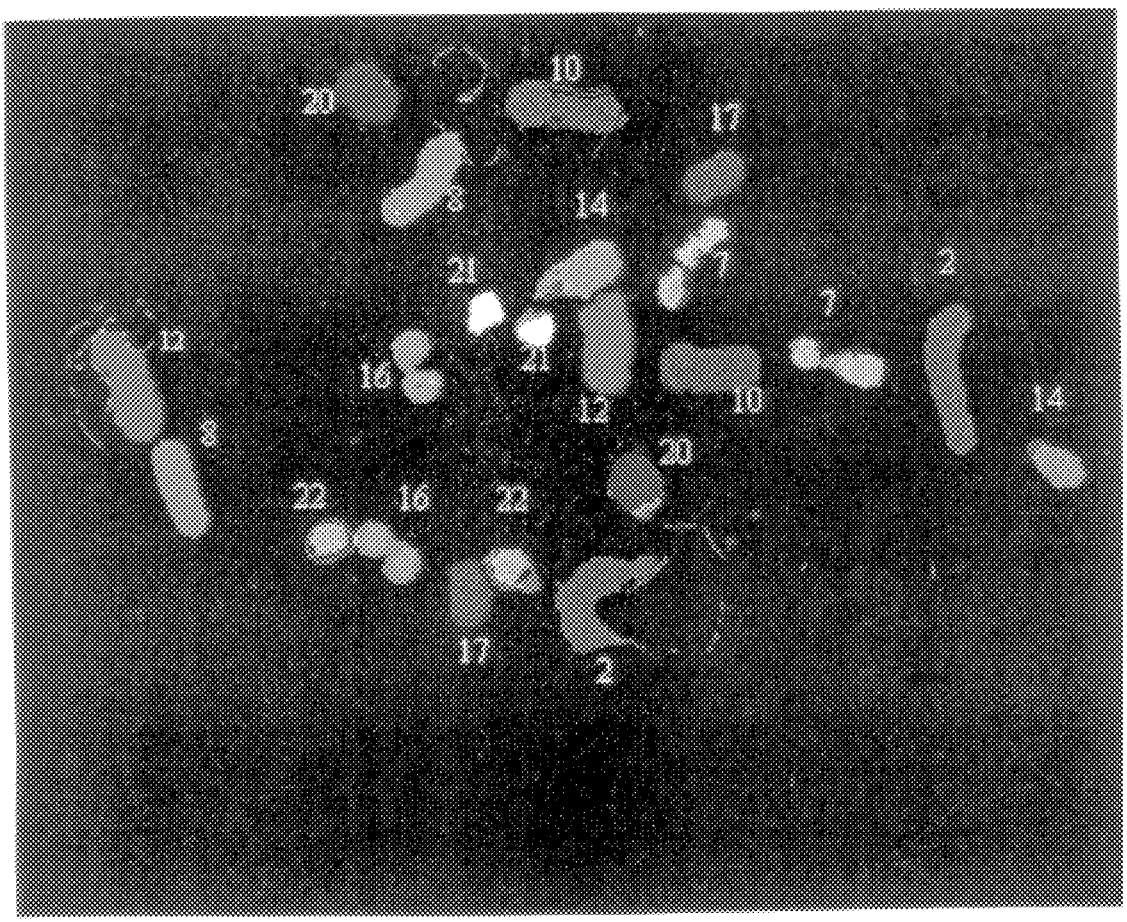
FIGS. 5a and 5b show the results of a simulated measurement followed by classification of pixels according to the method of the present invention implemented to classify combinatorially painted chromosomes of a normal human female (5a) and a male having a translocation involving chromosomes 16 and 9 (5b).
Figure 5B:
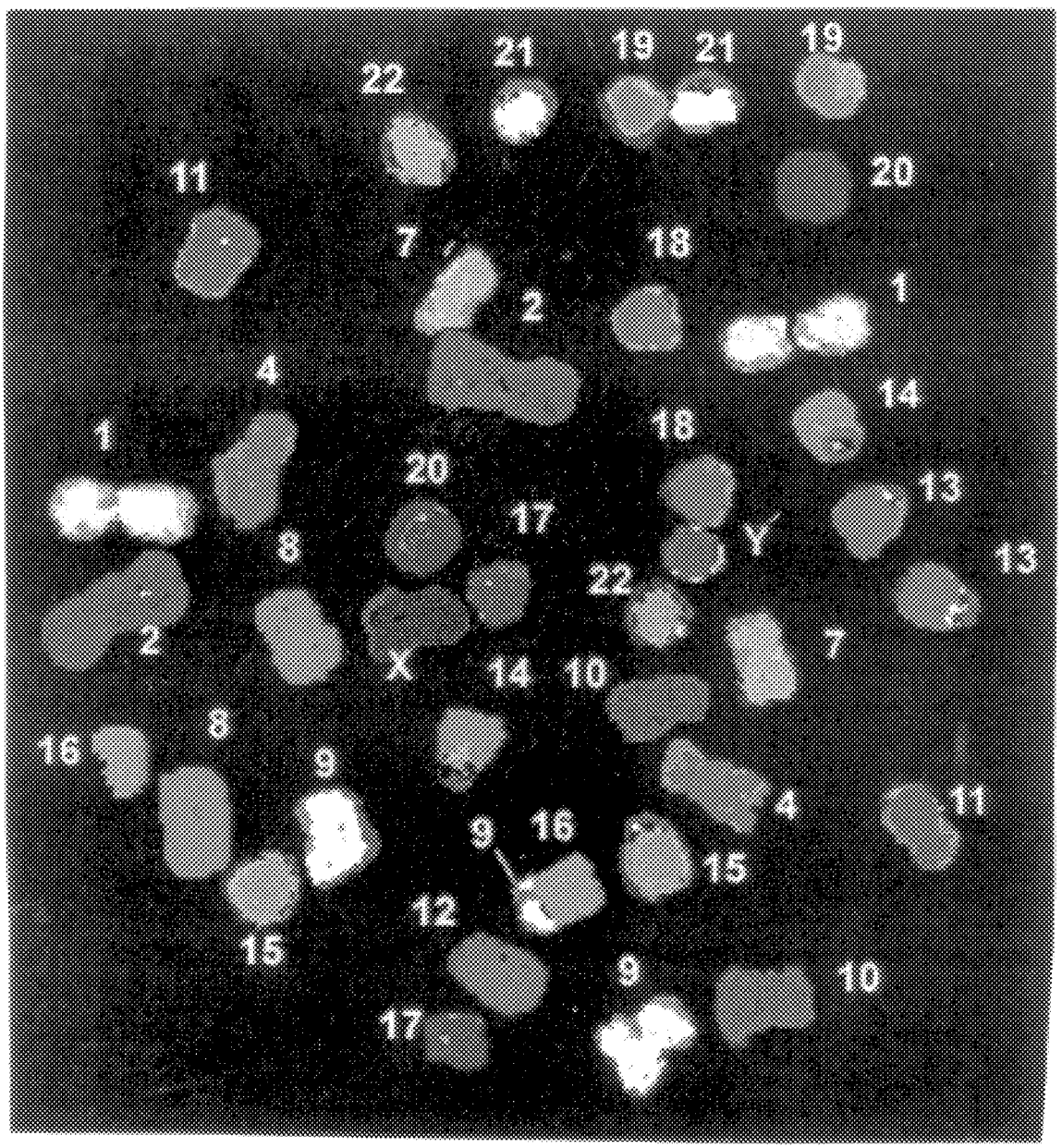

FIGS. 5a–b show partial metaphases prepared for analysis as described in Example 1 above using the following five dyes: SPECTRUM GREEN, SPECTRUM ORANGE, Texas Red, Cy5 and Cy5.5.

In the partial metaphase of FIG. 5a, which is of a normal female, five chromosomes are singly painted, one by each of the dyes, five chromosomes are doubly painted and one chromosome is quadruply painted. Table 5 provides the labeling scheme for each the chromosomes shown in FIG. 5a.

TABLE 5

| Chromosome | Spectrum Orange | Texas Red | Cy5 | Spectrum Green | Cy5.5 |
|---|---|---|---|---|---|
| 2 |  |  |  | + |  |
| 8 |  |  | + |  |  |
| 14 |  | + |  |  |  |
| 17 |  |  | + |  |  |
| 20 | + |  |  |  |  |
| 7 |  | + | + |  |  |
| 10 |  |  | + |  | + |
| 12 |  | + |  |  | + |
| 16 |  | + |  | + |  |
| 21 |  |  |  | + | + |
| 22 | + | + | + |  | + |

In the partial metaphase of FIG. 5b, which is of a male having a 16–9 translocation, five chromosomes are singly painted, one by each of the dyes, 9 chromosomes are doubly painted, 6 chromosomes are triply painted and 1 chromosome is quadruply painted. Table 6 provides the labeling scheme for each the chromosomes shown in FIG. 5b.

TABLE 6

| Chromosome | Spectrum Orange | Texas Red | Cy5 | Spectrum Green | Cy5.5 |
|---|---|---|---|---|---|
| 1 |  | + | + | + |  |
| 2 |  |  |  |  | + |
| 4 |  |  | + | + |  |
| 7 |  | + | + |  |  |
| 8 |  |  |  | + |  |
| 9 | + |  |  | + | + |
| 10 |  |  | + |  | + |
| 11 | + |  | + | + |  |
| 12 |  | + |  |  | + |
| 13 | + |  |  | + |  |
| 14 |  | + |  |  |  |
| 15 | + | + | + |  |  |
| 16 |  | + |  | + |  |
| 17 |  |  | + |  |  |
| 18 | + | + |  | + |  |
| 19 | + |  |  | + |  |
| 20 | + |  |  |  |  |
| 21 |  |  |  | + | + |
| 22 | + | + | + |  | + |
| X | + |  |  | + |  |
| Y |  |  | + | + | + |

It should be noted that the metaphase actual measurement which preceded simulation according to the method of the present invention was performed without using excitation and/or emission filters associated with any of the dyes as herein described in context of the invention.

The filter actually employed was a conventional triple dichroic filter cube (for excitation and emission) as described in, for example, E. Schroeck et al. (1996) Multi-color spectral karyotyping of human chromosomes. Science, 273, 494–497. As a direct result, the presence of wide excitation filters could not be simulated.

This fact has two effects on the results of the simulation.

First, the contemplated optimal results could not be obtained, because obviously the addition of excitation filters, if properly chosen, can only improve the specificity of the signals obtained from each dye, since the excitation spectrum of each dye is somewhat shifted with respect to the others while using such filters.

Second, some of the measured chromosomes, not shown here, had many pixels which could not be correctly identified following the simulation because of the reason set forth above.

However, it will be appreciated by one ordinarily skilled in the art that a relatively small increase of the signal of a dye due, for example, to the addition of its corresponding excitation filter in the optical path of the illumination would have corrected this effect.

The chromosome classification approach of the present invention as herein described may be employed for various applications some of which are detailed hereinbelow. Following is a brief summary of likely applications of the classification approach of the present invention in the field of molecular cytogenetics. Two major fields of cytogenetics in which the classification approach of the present invention will have considerable impact with particular emphasis on diagnostic applications are: (i) clinical cytogenetics and (ii) tumor cytogenetics.

First, the classification approach of the present invention may be used for diagnostic purposes to detect chromosomal aberrations in for example cancerous cells, fetal cells, etc., in a fashion similar to as described in U.S. patent application Ser. No. 08/635,820. About 400,000 cases in both clinical and cancer cytogenetics are analyzed each year in the United States alone, using conventional chromosome banding analysis. Chromosome painting using the classification approach of the present invention could be performed in addition to conventional banding analysis and would help to identify marker chromosomes that cannot be characterized using conventional banding alone. Acquired chromosomal aberrations are predominantly associated with malignant transformations. Roughly, two malignancies can be discerned: (i) hematological malignancies and (ii) solid tumors. Since the cells from hematological malignancies are easily cultured in vitro, the chromosome banding analysis of those tumors is one of the success stories in cytogenetic and genetic cancer research. Two well known examples include the identification of the Philadelphia chromosome in chronic lymphatic leukemia (CLL) and a specific chromosomal aberration in Burkitt's lymphoma. Many more tumor specific chromosomal aberrations were described in hematological malignancies in the last decade and are used as a diagnostic and research tool. In many cases the delineation of a recurrent chromosomal aberration has allowed to identify on a molecular basis the mechanism of malignant transformation. Disturbingly, less is known in the field of solid tumors (such as breast, colon, brain lung and other tumors). This discrepancy is even more disturbing because solid tumors play a much higher role in human morbidity than hematological malignancies. The discrepancy is mainly due to technical difficulties common in solid tumor cytogenetics. Solid tumors cells are often difficult to culture, the chromosome preparations are of poor quality, preventing a high resolution cytogenetic analysis, and secondary chromosomal aberration, not necessarily related to tumor initiation or progression are a common feature of these tumors. The availability of a hybridization based chromosomal screening test (i.e., chromosome painting) fills in a methodological gap and is as described above desperately required. Partly, comparative genomic hybridization helps in this respect. However, structural chromosomal aberration cannot be detected and always displays as average of chromosomal aberration in a cell mixture. It is very likely to predict that hybridization based karyotyping would become a widespread method for the delineation of recurrent chromosomal aberrations in solid tumors both in basic research and in the diagnostic laboratory.

Second, the classification approach of the present invention may be used for comparative cytogenetics [see, J. Weinberg and R. Stanyon (1995) Current opinion in genetics and development 5, 792–797], in a fashion similar to as described in U.S. patent application Ser. No. 08/635,820, to detect and visualize chromosomal rearrangements which changed chromosome morphology during evolution. In the study of evolutionary related species and in the study of model systems (for example mouse as a model system for human) it is in many cases required to obtain comparative genome maps in which chromosomes of two or more species are aligned according to their sequence similarities and thus their chromosome-borne genetic information. Using the classification approach of the present invention will facilitate obtaining such comparative maps. Consider for example the preparation of a human-mouse or human-ape chromosome comparative map. For this purpose a complete set of chromosome paints of one of the species (e.g., human) are to be simultaneously hybridized with chromosome spreads of the other species (mouse or ape in the given example) and classified as described above. The result is an image of the mouse karyotype painted with the human chromosome paints. Thus, an alignment can be made between the karyotypes of the two species.

Third, the classification approach of the present invention may be applied to cells during interphase, mitosis or meiosis. For example, this classification approach may be used to detect interphase chromosome three dimensional arrangements. Little is so far known about the chromosome organization during interphase, yet it is reasonable to suspect that changes occur in the chromosome organization during interphase in malignant cells. Thus, the classification approach of the present invention may be of great value for early detection of various malignancies, defining the stage of a malignant disease, and hence better adjust a treatment to examined patients, etc. It should be noted that using the classification method of the present invention in combination with a three dimensional reconstruction means (e.g., a confocal microscope) may be used to extract three dimensional information of chromosome organization during interphase, mitosis or meiosis.

Fourth, many cancers and genetic disorders are characterized by chromosome deletions, translocations and other rearrangements and gross abnormalities (e.g., gene amplification). Using the classification approach of the present invention will enhance the ability to detect such abnormalities.

Fifth, one of the common chromosomal aberrations is associated with Down's-syndrome. It was long ago established that Down's syndrome is associated with trisomy of chromosome 21. More careful examination revealed that a specific region of chromosome 21 (21q22) is always associated (i.e., appears in trisomy) with this common syndrome. However, in some cases the karyotype of individuals affected with Down's syndrome is apparently normal as determined by conventional G- or R-banding karyotyping techniques. The widely accepted explanation to this phenomenon is that in these cases the trisomy is of a fragment derived from the 21q22 chromosome region which fragment is small and below the resolution of the conventional banding techniques. However, using the classification method of the present invention will enable to detect these so far undetectable chromosome 21 trisomies in embryonic cells obtained for example via chorionic villi sampling and to enable a more educated genetic counseling to high risk women. It should be noted that chromosome 13 and chromosome 18 or fragments thereof were also reported to appear in trisomies resulting in birth of strikingly abnormal children and that the classification method of the present invention can be similarly applied for a prenatal diagnosis of these devastating chromosome 13 or 18 trisomies.

Sixth, the classification method of the present invention, combined with the rapidly developing techniques of separating embryonic cells from peripheral blood of a pregnant woman will be of great value for low-risk prenatal karyotyping for the detection of chromosome 21 trisomies and other less frequent chromosome abnormalities.

Seventh, the classification method of the present invention can be used for the generation of a multicolor banding pattern of chromosomes (i.e., bar-coding, multicolor banding karyotype). For details regarding chromosome bar coding the reader is referred to C. Lengauer et al. (1993) Hum. Molec. Genet. 5, 505–512. The first goal of the human genome project (HGP) is about to be completed. This goal is the generation of a physical map of the human genome. The term physical map refers to the cloning of the entire genome in large insert vectors such as YAC-clones or BAC-clones and the mapping of these clones by means of genetic, cytogenetic and physical mapping. Two major sources of human DNA were used (for this endeavor, radiation hybrid cell lines and YAC-contigs that contain overlapping clones for all human chromosomes. The completion of this map allows to retrieve for virtually every region in the genome specific clones that are required to identify genes that are causally involved in inherited or acquired genetic diseases including cancer. By combining FISH with multiple YAC- or BAC-clones or radiation hybrids and spectral imaging it is possible to generate a multicolor banding pattern for all human chromosomes that will ultimately link the genetic and the cytogenetic map. As an example, consider the use of a radiation hybrid panel (Stanford panel) [see, Barret J. H. (1992) Genetic mapping based on radiation hybrids. Genomics 13, 95–103]. Each individual panel of the Stanford panel contains a set of DNA fragments with an average fragment size of ca. 5,000 kbp. Each individual panel covers ca. 20% of the human genome. The cohybridization of fluorescent probes derived from five such panels would therefore result in coverage of most of the genome and thus labeling of all human chromosomes. However, the fragments are randomly distributed in the individual panels. Therefore, the number of panels that are required for a complete coverage of the human genome is higher (e.g., 6–10 panels). In the following description assumed is that five individual panels are used. The chromosome fragments of each of the panels are labeled with a different fluorophore (or a different combination of fluorophores, e.g., combinatorial labeling or hybridization strategies) by for example directly incorporating dUTP-conjugated fluorophores using primers derived from interspersed repetitive sequences (IRS, e.g., Alu sequences) in a method known in the art as IRS-PCR approach such as Alu-PCR, which guarantees an exclusive amplification and labeling of human sequences only. If DNA from a species other than human is to be thus amplified and or labeled, a species specific interspersed repetitive sequence (IRS) characterizing the genome of that species is to be used to derive suitable PCR primers. A single separate hybridization of one of the individual panels would give a banding pattern of a chromosome spread in one color with a coverage of about 20% of the genome and an average band size of 5,000 Kbp.

Due to the random overlap of individual chromosome fragments in the five hybrid panels, the cohybridization of five differentially labeled groups (each group is represented by a single panel) of fragments would result in a banding pattern including bands that have pure colors, bands that include a combination of two, three, four, as well as five colors each, collectively 31 possible color combinations, which combinations can be distinguished using spectral imaging. To this end, a preprocess for classification should be performed in a similar fashion to as described above to obtain, in the given example, 31 different N-dimension vectors, one for each of the 31 color combinations. Classification of new samples can then be performed essentially as described hereinabove. It is clear that describing 31 color combinations is for illustrative purposes only and that any other suitable number of combinations is included in the scope of the present invention. The generation of a multicolor high resolution banding pattern of chromosomes has two distinct advantages as compared to the use of chromosome painting probes (i.e., chromosome paints) as follows. Chromosome painting is a well suited tool to detect interchromosomal aberrations such as translocation or homogeneously staining regions as well as additional chromosomes material such as marker chromosomes or double minute chromosomes. Intrachromosomal aberrations such as deletions and duplications would be detected only if the size of the aberrations affect the length of the chromosomes, whereas chromosomal inversions are not detectable at all by this method. However utilizing a multicolor banding pattern, inter- as well as intrachromosomal aberrations could be diagnosed because they would affect the sequence of the chromosomal bands. One major advantage of multicolor high resolution banding pattern using pre-mapped DNA fragments (e.g., YAC-clones and radiation hybrids cell lines) is the possibility to integrate the genetic and the cytogenetic map. Each multicolor band is characterized by a specific set of sequence tagged sites. These are PCR products that occur only once in the genome. Following is a description of the usefulness of the integrated cytogenetic and genetic map. For example, the lack of a specific color band on a chromosome derived from a tumor cell is indicative of a microdeletion that often reflects the loss of a tumor suppressor gene. The knowledge of the sequence target sites (STS's) that are specific for this band would allow to screen any large insert clone collection and retrieve a number of specific clones that are highly likely to contain the gene that is deleted in the described example. It should be mentioned that with the large scale sequencing efforts now underway and with the integration of expressed tagged sites (loci that are known to contain a gene) the value of a hybridization based multicolor banding pattern would increase even more. It is also conceivable that such a multicolor banding pattern could be readily automated. Despite considerable efforts automation of cytogenetic diagnosis based on conventional chromosome bands was so far not successful. The approach described hereinabove will not only be applicable for the generation of a hybridization based banding pattern of human chromosomes but also for other mammalian (e.g., mouse) and non-mammalian species. This will be particularly useful for the analysis in animal models of human diseases including cancer. In analogy to the scenario described for the radiation hybrid panels, a multicolor banding pattern for all human chromosome could be achieved by cohybridization of a set on individual large insert clones such as YAC-clones, P1-clones, BAC-clones or, depending on the resolution that is desired the use of contigs (overlapping clones) from these sources. In further analogy to the use of radiation hybrid panels, a multicolor banding pattern could be introduced by deliberately labeling overlapping clones or contigs with different fluorophores. All advantages of the hybridization based chromosome banding approach has as compared to the use of chromosome paints or to conventional chromosome banding described above, applies to usage of large inserts clones as well. It will be appreciated by one ordinarily skilled in the art that the retrieval of clones involved in chromosome breakpoints or in chromosomal deletion would be even more straightforward than with the use of radiation hybrid panels. Another source of chromosome fragments suitable for use for multicolor chromosome banding are fragments obtained by microdissection of chromosomes. Microdissected chromosomes fragments are generated by manual or laser micromanipulation of chromosome spreads as well known in the art. The fragments thus produced are typically multiplied by polymerase chain reaction using for example degenerated oligonucleotides primers (DOP) in a method known in the art as DOP-PCR, or using primers derived from interspersed repetitive sequences (IRS, e.g., Alu sequences) in a method known in the art as IRS-PCR. Yet, an additional source of chromosome fragments suitable for use for multicolor chromosome banding are fragments generated by DNA restriction approaches that generate large DNA fragments and electrophoresis approaches capable of size separating large DNA fragments. As far as generating large DNA fragments by DNA restriction two approaches may be considered. According to the first, a partial digestion by an endonuclease (e.g., frequent or rare cutter) is used, whereas according to the second, a complete digestion by a rare cutter endonuclease (e.g., NotI), is used. The latter is presently preferred, since a complete digestion can be repeated to yield identical results in independent trials, whereas partial digestion is random in nature. Electrophoresis approaches capable of size separating large DNA fragments are well known in the art and include pulse field gel electrophoresis (PFGE). Thus, for example, extracting DNA from consecutive regions along a PFGE lane, labeling the DNA extracted from each of the regions using a different fluorophore and cohybridizing thus formed probes to chromosomes, would result in a multicolor banding pattern of the chromosomes similarly to as described above. Large DNA fragments may additionally be obtained via gradient centrifugation such as sucrose or cesium chloride gradients as well known in the art. Nevertheless, it will be appreciated that using these approaches do not provide a possibility to integrate the genetic and the cytogenetic map as described above and is therefore presently less favorable. The generation of a multicolor banding pattern of chromosomes (i.e., multicolor banding karyotype) based on fluorescent in situ hybridization and the classification approach of the present invention can be used for various practical applications. These include for example (i) screen for chromosomal aberrations using for example specifically tailored clone sets; (ii) screening for telomeric deletions, which are otherwise difficult of detection; (iii) screening for chromosomal aneuploidies during prenatal diagnosis; (iv) screening for recurrent chromosomal breakpoints; (v) multicolor comparative genomic hybridization; (vii) combining multicolor FISH with other measurements of cytological and immunohistochemical stains for multiparameter analysis of tumor cells; (viii) combining multicolor banding patterns with conventional R- or G-bands; (ix) analysis of genetic aberrations directly in interphase cells; and (x) screening for chromosomal aberrations in radiation or mutagen exposed populations.

Eighth, the classification approach of the present invention can be expanded to include a morphological algorithm, as well known in the art of automatic karyotyping, to achieve even better results.

FIG. 5a and 5b present two examples of partial metaphases analyzed according to the method of the present invention. The basic steps of the analysis described in this example were all used to obtain the results shown in FIGS. 5a–b with some additional steps of morphological nature to improve the quality of the results.

Following is a more detailed account of the analytical steps, starting from the simulation of the measurements until the display of the results.

1. The measurement is simulated using the integrals of the spectra measured with an apparatus described in Example 2 on a cube A of a metaphase prepared according to Example 1. The dyes used in the hybridization are those of Table 1, the dye combinations are those of Table 2, and 5 spectral integrals for each pixel are calculated over the ranges of the 5 emission filters listed in Table 4, forming a 5-dimensional vector for each pixel.
2. The average integrals of the spectra belonging to the previously known singly stained chromosomes are stored in a library and used as the known coefficients $R_i^j$ of Equations 1 and 2.
3. The spatial resolution of cube A is reduced by, for example, a 3×3 pixel spatial filtering of the data (reducing the spatial noise), yielding a new cube B.
4. A local "background" cube C is calculated by, for example, a 30×30 pixel spatial filtering of cube A and subtracted from cube B forming a new cube D to take into account local intensity variations due to scattering and other sources of unwanted radiation.
5. Since negative data are not physical, all the data of cube D are thresholded at zero, yielding a new cube E of 5-vectors of only positive component values.
6. The new 5-dimensional vectors of cube E so obtained for all the pixels and the $R_i^j$ data of the singly stained pixels are used in Equations 1 and 2 as explained above, to find the 5-vectors $n_i/N_i$ (i=1, . . . 5) for each pixel.
7. For each pixel, the values of $n_i/N_i$ are thresholded respectively at 0.13, 0.2, 0.2, 0.3, and 0.3, obtaining new 5-vectors which are made of combinations of zeros and non-zero elements, and this new cube is called G.
8. Each pixel of cube G is compared to the dye combinations listed in Table 2, with the following rules: (i) the presence or absence of dyes a, b, c, d, and e in a pixel are indicated respectively by the first, second, third, fourth and fifth components of the 5-vectors of G; (ii) if a component equals zero, its corresponding dye is absent; (iii) if a component is not zero, its corresponding dye is present; (iv) Table 2 gives the translation from the presence-absence vector of a pixel to the correct chromosome number to which it belongs.
9. The image so obtained is displayed on the computer screen with each chromosome number shown in a predetermined color as exemplified in FIGS. 5a and 5b. The chromosomes may thereafter be rearranged in pairs to form a karyotype (not shown), as well known in the art.

EXAMPLE 4

AOTFs and LCTFs

Tunable filters (TFs), such as acousto-optic tunable filters (AOTFs) and liquid-crystal tunable filters (LCTFs), are solid state electronically tunable spectral bandpass selectors having no moving parts which can be electronically tuned to any particular wavelength, as well known in the art. As such, a tunable filter can be thought of as a variable bandpass filter that can be electronically tuned to any wavelength over its range.

A liquid-crystal tunable filter (LCTF) is a solid state electronically tunable spectral bandpass filter typically made of high molecular weight organic substances having a dipole. Tuning LCTF is performed by subjecting the liquid crystal to varying electrical voltages. LCTF is a birefringent filter that uses phase retardation to create constructive and destructive interference. By stacking a number of stages in series, a single bandpass is obtained in a manner similar to that of a multicavity interference filter. LCTF technology was introduced by Cambridge Research & Instrumentation (CRI) Inc. in 1992. The first generation LCTFs produced suffered various limitations as for as bandpass width and shape and transmission of polarized and especially of randomly-polarized light are concerned. However, second generation LCTFs have overcome these problems enabling transmission of about 100 percent of polarized light, substantially greater than 50 percent of randomly-polarized light, broad bandpass (top and bottom) of variety of shapes in the spectral range of 400 nm to 720 nm. To the development in LCTFs the reader is referred to Clifford Hoyt (1996) Liquid crystals tunable filters clear the way for imaging multiprobe fluorescence. Biomotonics International, 3(4), 49–51. Further information concerning LCTF can be found in for example Hoyt and Benson (1992) Merging spectroscopy and digital imaging enhances cell research. Photonics Spectra 26(11), 92–97; Kopp (1994) Tunable birefringent filters using liquid crystal variable retarders. Proc. SPIE 2265, 192–201; Miller and Hoyt (1995) Multispectral imaging with a liquid crystal tunable filter. Proc. SPIE 2345, 354–365; and Koenig et al. (1994) In-vivo fluorescence detection and imaging of porphyrin-producing bacteria in the human skin and in the oral cavity for diagnosis of acne, caries, and squamous cell carcinoma. Proc. SPIE 2135, 129–138, all are incorporated by reference as if fully set forth herein.

An acousto-optic tunable filter (AOTF) is a solid state electronically tunable spectral bandpass filter which can be operated from the ultra violet through the visible and into the infrared regions of the optical spectrum. The AOTF operates on the principle of acousto-optic interaction in an anisotropic medium. In other words the AOTF functions by the interaction of light with traveling acoustic wave through the medium, which creates a periodic modulation of its index of refraction by means of the elasto-optic effect. This modulation acts as a three-dimensional sinusoidal phase grating for light incident upon the crystal, leading to the diffraction of certain wavelengths at an angle from the incident beam radiation. To this end, an acoustic transducer, typically a piezoelectric motor, is bonded to one face of the crystal and an acousto absorber is typically bonded to an opposite face. The transducer converts a high frequency rf (radio frequency) signal into a sinusoidal pressure wave which propagates laterally through the crystal. As a result, the medium operates similar to a grating, wherein incident light is diffracted to its spectral wavelengths, light of varying wavelengths is acquired different angles with respect to the incident light beam when leaving the medium as a throughput. The acoustic absorber at the opposite end of the crystal eliminates acoustic reflections which would corrupt the primary acoustic wave form. The conservation of momentum between the incident and diffracted photon wave vectors and the acoustic wave vector determines the wavelength of the diffracted light passing the medium at a given angle. Thus, without moving the AOTF, one can control the wavelength of light that will pass the medium in a selected angle. Optical tuning, or in other words the wavelength of light which passes the medium in a preselected angle, is achieved by selecting the rf frequency signal.

The use of AOTFs for spectroscopic applications and for spectral imaging applications is not new, see for example U.S. Pat. Nos. 5,216,484 to Chao et al. 5,377,003 to Lewis et al. Further information concerning the operation of AOTFs can be found in for example Wang and Lewis (1996) Acousto-optic tunable filters and their application in spectroscopic imaging and microscopy. In, "Fluorescence Imaging Spectroscopy and Microscopy". Feng, Wang and Brian, Eds. John Wiley and Sons Inc.; Harris et al. (1969) Acousto-optic tunable filters. Journal of the optical society of America, 59, 744–747; Chang (1977) Noncolinear acousto-optic filter with large angular aperture. Applied Physics Letters, 25, 370–372; Eliot et al. (1996) Imaging acousto-optic tunable filter with 0.35-micrometer spatial resolution. Applied Optics, 35, 5220–5226; and in U.S. Pat. Nos. 3,679,288; 3,944,334; 3,944,335; 3,953,107; 4,052,121; 4,342,502 and 5,039,855, all are incorporated by reference.

Traditionally AOTFs were used to generate a varying narrow bandpass, Nevertheless, electronically controlling the acouso wave parameters by, for example, superposition (e.g., linear combination) of acoustic waves of different wavelengths and/or different amplitudes, by, for example, employing more than one transducer, enables to select any desired wave pattern that results in passing different intensities of light at variable wavelengths in a preselected angle. Furthermore, by omitting the acousto absorber to allow the presence and therefore superposition of waves reflected from the end face of the crystal can also be used to control passage of different intensities of light at variable wavelengths in the preselected angle. Thus, when driven with multiple closely spaced rf's, the AOTF also provides electronically variable bandpass and shape control. To this effect the reader is referred to Eliot et al. (1996) Imaging acousto-optic tunable filter with 0.35-micrometer spatial resolution. Applied Optics, 35, 5220–5226.

Thus, any of the wide bandpass excitation and emission filters required to implement the method of the present invention may be represented by a single tunable filter, alternatively by a subset of few filters, which collectively, when sequentially applied for measurement, yield otherwise substantially identical results. Any such combination of filters may be implemented by a single tunable filter (LCTF or AOTF) which can be tuned at a different bandpass to sequentially implement any of the required filters.

It will be appreciated that by using tunable filters such as AOTF and LCTF, a single filter is required for measurement, the tunable filter is tuned to change its spectral characteristics in a manner that sequentially follows any desired characteristics. Thus for measurement of in situ hybridized chromosomes, tuning information is selected such that the tunable filter sequentially implements the wide-band excitation and emission filters. This, however implies that the measurement involves no moving parts as it is electronically controlled.

EXAMPLE 5

A Wide-Band Excitation and Emission Filters Apparatus

As described above, employing wide-band excitation and emission filters which compensate for loss of specificity by gain of throughput, or which compensate for loss of throughput by gain of specificity may be used for classification of pixels into groups.

Figure 6:
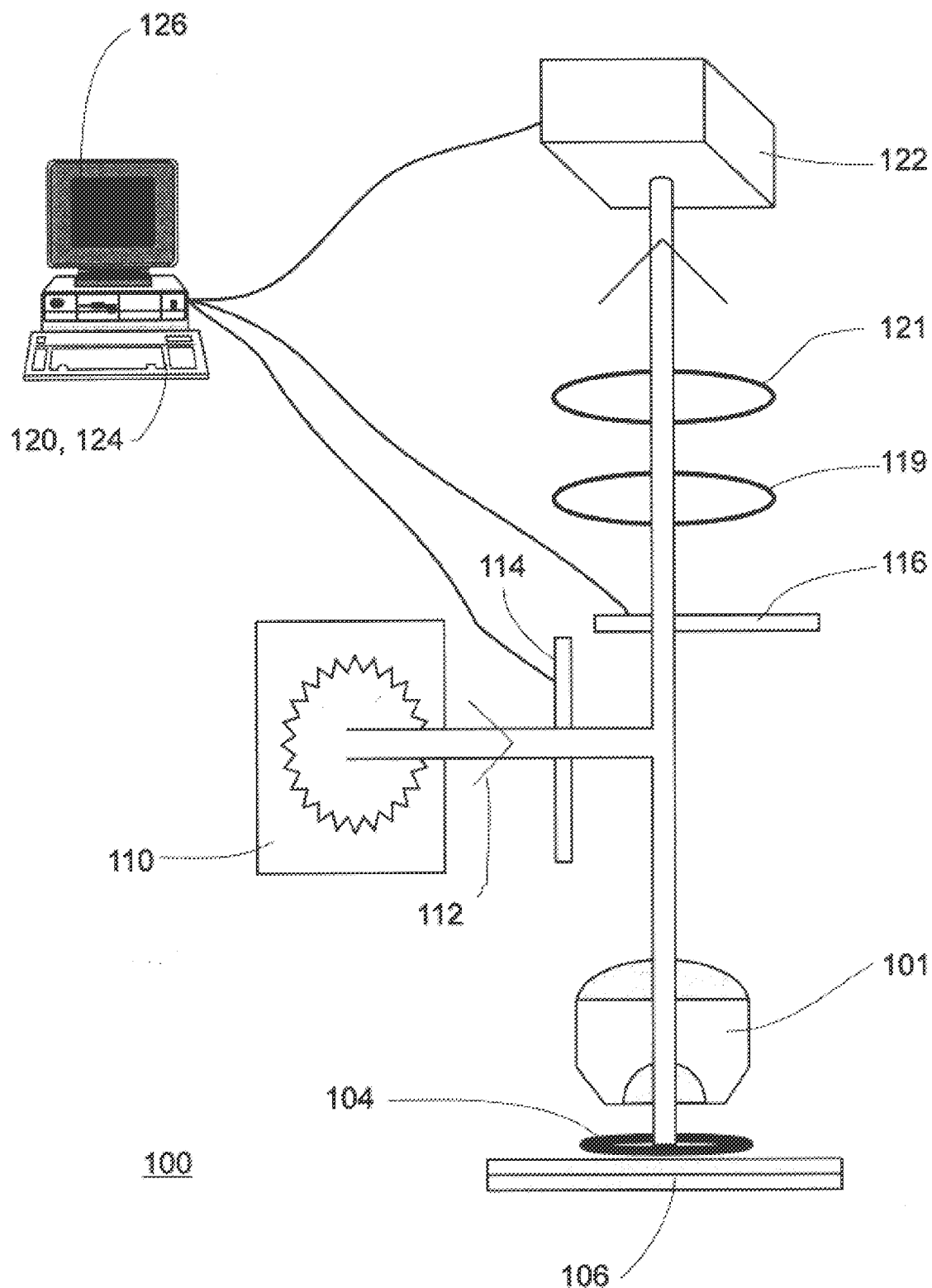
FIG. 6 is a schematic depiction of a device including conventional filters suitable to implement the method of the present invention.

With reference now to FIG. 6. For ease of measurement pairs of excitation and emission filters are placed in an apparatus referred to hereinbelow as apparatus 100. Apparatus 100 serves for classification of pixels into groups of pixels according to their association with a single fluorophore or a combination of fluorophores selected from a plurality of fluorophores. Each of the fluorophores has characterizing excitation and emission spectra and specifying excitation and emission peaks. For classification, a sample of, for example, in situ painted chromosomes 104, which corroborates with the above description is placed under an objective 101 of apparatus 100, on a supporting plane 106.

Apparatus 100 includes a light source 110 which provides a light beam 112. Beam 112 includes light in the wavelengths range suitable to excite the fluorophores of choice.

Apparatus 100 further includes a plurality of pairs of wide-band excitation filters 114 and wide-band emission filters 116, five pairs are shown. The filters enjoy the above described features. Filters 114 serve to restrict the illumination provided by light beam 112 to specific excitation wavelengths which compensate between excitation throughput and specificity as described above. Filters 116 serve to restrict the light emitted from sample 104 to specific wavelengths to compensate between emission throughput and specificity as described above.

Apparatus 100 further includes an automatic, manual or semimanual control device 120. Device 120 serves for selecting a pair of filters 114 and 116, for exciting fluorophores of each of the pixels with light originating from light source 110 filtered through one of the wide-band excitation filters 114, and for repeating the above procedure for all of the filter pairs.

Apparatus 100 further includes a light intensity recording device 122 (e.g., a CCD) which serves for recording emitted light intensity as retrieved after passing through emission filters 116.

As a result each of the pixels is representable by a vector of a plurality of dimensions, the number of dimensions being equal to the number of the plurality of pairs of filters 114 and 116.

Apparatus 100 further includes a computing device 124. Device 124 includes an algorithm for evaluating the presence of each of the plurality of fluorophores in each of the pixels.

Thereby, computing device 124 serves for classifying each of the pixels into a group of pixels according to its association with a single fluorophore or any of the combinations of fluorophores.

In a preferred embodiment computing device 124 serves for giving pixels belonging to each of the groups of pixels a unique artificial color, such that pixels belonging to each of the groups are distinguishable from one another.

Apparatus 100 preferably further includes a display 126 (e.g., a computer screen) for presenting the results of the classification by the artificial colors.

In a preferred embodiment apparatus 100 further includes a collimating lens 119 to ensure full collimation of the light before reaching recording device 122.

In a preferred embodiment apparatus 100 further includes a focusing lens 121 for focusing light reaching recording device 122.

It will be appreciated by one ordinarily skilled in the art that using apparatus 100 according to the present invention is beneficial for all the cytogenetic applications based on the classification approach of the present invention as delineated under Example 6 above, especially for chromosome banding analysis.

EXAMPLE 6

A Wide-Band Excitation and Emission AOTF and LCTF Filters Apparatus

As described above, the wide-band excitation and emission filters which compensate for loss of specificity by gain of throughput, or which compensate for loss of throughput by gain of specificity may be replaced by tunable filters.

Figure 7:
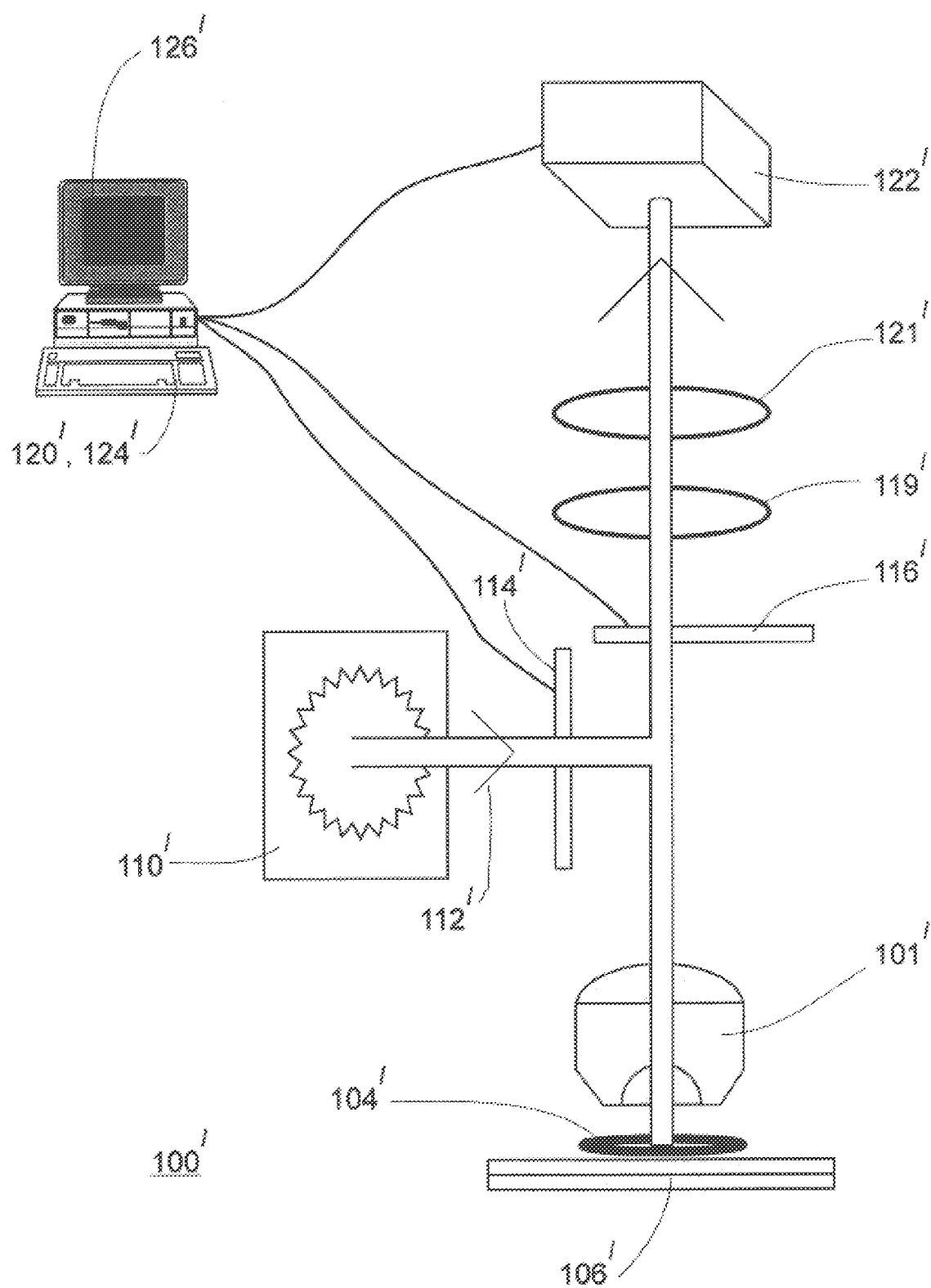
FIG. 7 is a schematic depiction of a device including tunable filters suitable to implement the method of the present invention.

With reference now to FIG. 7. For ease of measurement a pair of excitation and emission tunable filters are placed in an apparatus referred to hereinbelow as apparatus 100'. As before, apparatus 100' serves for classification of pixels into groups of pixels according to their association with a single fluorophore or a combination of fluorophores selected from a plurality of fluorophores. Each of the fluorophores has characterizing excitation and emission spectra and specifying excitation and emission peaks. For classification, a sample of, for example, in situ painted chromosomes 104', which corroborates with the above description is placed under an objective 101' of apparatus 100', on a supporting plane 106'.

Apparatus 100' includes a light source 110' which provides a light beam 112'. Beam 112' includes light in the wavelengths range suitable to excite the fluorophores of choice.

Apparatus 100' further includes a pair of filters including a wide-band tunable excitation filter 114' and a wide-band emission filter 116'. The filters are tunable and therefore may be tuned to sequentially represent the pairs of conventional bandpass filters used in apparatus 100' of Example 5 (FIG. 6). Thus, filter 114' serves to restrict the illumination provided by light beam 112' to specific excitation wavelengths which compensate between excitation throughput and specificity as described above. Filter 116' serves to restrict the light emitted from sample 104' to specific wavelengths to compensate between emission throughput and specificity as described above.

Apparatus 100' further includes a control device 120'. Device 120' serves for tuning filters 114' and 116', for exciting fluorophores of each of the pixels with light originating from light source 110' filtered through excitation filter 114', and for repeating the above procedure after retuning.

Apparatus 100' further includes a light intensity recording device 122' (e.g., a CCD) which serves for recording emitted light intensity as retrieved after passing through emission filter 116'.

As a result each of the pixels is representable by a vector of a plurality of dimensions, the number of dimensions being equal to the number of tuning situations imposed by filters 114' and 116'.

Apparatus 100' further includes a computing device 124'. Device 124' includes an algorithm for evaluating the presence of each of the plurality of fluorophores in each of the pixels.

Thereby, computing device 124' serves for classifying each of the pixels into a group of pixels according to its association with a single fluorophore or any of the combinations of fluorophores.

In a preferred embodiment computing device 124' serves for giving pixels belonging to each of the groups of pixels a unique artificial color, such that pixels belonging to each of the groups are distinguishable from one another.

Apparatus 100' preferably further includes a display 126' (e.g., a computer screen) for presenting the results of the classification by the artificial colors.

In a preferred embodiment apparatus 100' further includes a collimating lens 119' to ensure full collimation of the light before reaching recording device 122'.

In a preferred embodiment apparatus 100' further includes a focusing lens 121' for focusing light reaching recording device 122'.

It will be appreciated by one ordinarily skilled in the art that using apparatus 100' according to the present invention is beneficial for all the cytogenetic applications based on the classification approach of the present invention as delineated under Example 3 above, especially for chromosome banding analysis.

While the invention has been described with respect to a limited number of embodiments, it will be appreciated that many variations, modifications and other applications of the invention may be made.

What is claimed is:

1. A method of classification of pixels into groups of pixels according to their association with a single fluorophore or a combination of fluorophores selected from a plurality of fluorophores, each of the fluorophores having characterizing emission spectrum and specifying emission peak, the method comprising the steps of:

(a) providing a plurality of wide-band emission filters;

(b) for each of the pixels, recording emitted light intensity as retrieved after passing through each one of said plurality of emission filters, such that each of the pixels is representable by a vector of a plurality of dimensions, the number of dimensions being equal to the number of plurality of wide-band emission filters;

(c) using an algorithm for evaluating the presence of each of the plurality of fluorophores associated with each of the pixels, thereby classifying each of the pixels into a group of pixels according to its association with a single fluorophore or combination of fluorophores.

2. The method of claim 1, wherein at least two of said plurality of wide-band emission filters have overlapping bandpasses.

3. The method of claim 1, wherein pixels belonging to each of said groups of pixels are given a unique artificial color, such that pixels belonging to each of said groups are distinguishable from one another.

4. The method of claim 1, wherein said algorithm is a linear decomposition algorithm.

5. The method of claim 1, wherein said fluorophores are bound to genetic material of metaphase chromosomes, such that genetic material of each of said metaphase chromosomes is bound to a different fluorophore or combination of fluorophores.

6. The method of claim 5, wherein the number of said plurality of fluorophores is five.

7. The method of claim 6, wherein the number of said plurality of wideband emission filters is five.

8. The method of claim 1, wherein the number of said plurality of fluorophores equals the number of said plurality of wide-band emission filters.

9. The method of claim 1, wherein each of said plurality of wide-band filters is selected to have a bandpass corresponding to said emission spectrum of one fluorophore of said plurality of fluorophores and to thereby allow a high throughput of light emitted from said one fluorophore.

10. The method of claim 9, wherein said bandpass of at least one of said plurality of wide-band filters is selected to overlap with said emission peak of its corresponding fluorophore.

11. The method of claim 1, wherein said plurality of wide-band filters are represented by a single tunable filter.

12. The method of claim 11, wherein said tunable filter is selected from the group consisting of acousto-optic tunable filter and liquid-crystal tunable filter.

13. A method of classification of pixels into groups of pixels according to their association with a single fluorophore or a combination of fluorophores selected from a plurality of fluorophores, each of the fluorophores having characterizing excitation and emission spectra and specifying excitation and emission peaks, the method comprising the steps of:
  (a) providing a plurality of pairs of wide-band excitation filters and wide-band emission filters;
  (b) exciting fluorophores of each of the pixels with light filtered through one of said wide-band excitation filters, and recording emitted light intensity as retrieved after passing through its paired emission filter;
  (c) repeating step (b) for all of said plurality of pairs of filters, such that each of the pixels is representable by a vector of a plurality of dimensions, the number of dimensions being equal to the number of said plurality of pairs of filters;
  (d) using an algorithm for evaluating the presence of each of the plurality of fluorophores associated with each of the pixels, thereby classifying each of the pixels into a group of pixels according to its association with a single fluorophore or combination of fluorophores.

14. The method of claim 13, wherein at least two of said wide-band emission filters have overlapping bandpasses.

15. The method of claim 13, wherein at least two of said wide-band excitation filters have overlapping bandpasses.

16. The method of claim 14, wherein at least two of said wide-band excitation filters have overlapping bandpasses.

17. The method of claim 13, wherein pixels belonging to each of said groups of pixels are given a unique artificial color, such that pixels belonging to each of said groups are distinguishable from one another.

18. The method of claim 13, wherein said algorithm is a linear decomposition algorithm.

19. The method of claim 13, wherein said fluorophores are bound to genetic material of metaphase chromosomes, such that genetic material of each of said metaphase chromosomes is bound to a different fluorophore or combination of fluorophores.

20. The method of claim 19, wherein the number of said plurality of fluorophores is five.

21. The method of claim 20, wherein the number of said plurality of pairs of filters is five.

22. The method of claim 13, wherein the number of said plurality of fluorophores equals the number of said plurality of pairs of filters.

23. The method of claim 13, wherein each of said wide-band emission filters is selected to have a bandpass corresponding to said emission spectrum of one fluorophore of said plurality of fluorophores and to thereby allow a high throughput of light emitted from said one fluorophore.

24. The method of claim 13, wherein each of said wide-band excitation filters is selected to have a bandpass corresponding to said excitation spectrum of one fluorophore of said plurality of fluorophores and to thereby allow a high throughput of excitation light.

25. The method of claim 23, wherein said bandpass of at least one of said wide-band emission filters is selected to overlap with said emission peak of its corresponding fluorophore.

26. The method of claim 24, wherein said bandpass of at least one of said wide-band excitation filters is selected to overlap with said excitation peak of its corresponding fluorophore.

27. The method of claim 13, wherein said wide-band emission filters are represented by a single tunable filter.

28. The method of claim 27, wherein said tunable filter is selected from the group consisting of acousto-optic tunable filter and liquid-crystal tunable filter.

29. The method of claim 13, wherein said wide-band excitation filters are represented by a single tunable filter.

30. The method of claim 29, wherein said tunable filter is selected from the group consisting of acousto-optic tunable filter and liquid-crystal tunable filter.

31. An apparatus for classification of pixels into groups of pixels according to their association with a single fluorophore or a combination of fluorophores selected from a plurality of fluorophores, each of the fluorophores having characterizing excitation and emission spectra and specifying excitation and emission peaks, the apparatus comprising:
  (a) a light source;
  (b) a plurality of pairs of wide-band excitation filters and wide-band emission filters;
  (c) a control device for:
    (i) selecting a pair of said plurality of pairs;
    (ii) exciting fluorophores of each of the pixels with light originating from said light source filtered through one of said wide-band excitation filters; and
    (iii) repeating steps (i)–(ii) for all of said plurality of pairs of filters, such that each of the pixels is representable by a vector of a plurality of dimensions, the number of dimensions being equal to the number of said plurality of pairs of filters;
  (d) a light intensity recording device for recording emitted light intensity as retrieved after passing through said emission filters; and
  (e) a computing device including an algorithm for evaluating the presence of each of the plurality of fluorophores associated with each of the pixels, thereby classifying each of the pixels into a group of pixels according to its association with a single fluorophore or combination of fluorophores.

32. The apparatus of claim 31, wherein at least two of said wide-band emission filters have overlapping bandpasses.

33. The apparatus of claim 31, wherein at least two of said wide-band excitation filters have overlapping bandpasses.

34. The apparatus of claim 32, wherein at least two of said wide-band excitation filters have overlapping bandpasses.

35. The apparatus of claim 31, wherein said computing device serves for giving pixels belonging to each of said groups of pixels a unique artificial color, such that pixels belonging to each of said groups are distinguishable from one another.

36. The apparatus of claim 31, wherein said algorithm is a linear decomposition algorithm.

37. The apparatus of claim 31, wherein the number of said plurality of pairs of filters is five.

38. The apparatus of claim 31, wherein the number of said plurality of fluorophores equals the number of said plurality of pairs of filters.

39. The apparatus of claim 31, wherein each of said wide-band emission filters is selected to have a bandpass corresponding to said emission spectrum of one fluorophore of said plurality of fluorophores and to thereby allow a high throughput of light emitted from said one fluorophore.

40. The apparatus of claim 31, wherein each of said wide-band excitation filters is selected to have a bandpass corresponding to said excitation spectrum of one fluorophore of said plurality of fluorophores and to thereby allow a high throughput of excitation light.

41. The apparatus of claim 39, wherein said bandpass of at least one of said wide-band emission filters is selected to overlap with said emission peak of its corresponding fluorophore.

42. The apparatus of claim 40, wherein said bandpass of at least one of said wide-band excitation filters is selected to overlap with said excitation peak of its corresponding fluorophore.

43. The apparatus of claim 31, wherein said wide-band emission filters are represented by a single tunable filter.

44. The apparatus of claim 43, wherein said tunable filter is selected from the group consisting of acousto-optic tunable filter and liquid-crystal tunable filter.

45. The apparatus of claim 31, wherein said wide-band excitation filters are represented by a single tunable filter.

46. The apparatus of claim 45, wherein said tunable filter is selected from the group consisting of acousto-optic tunable and liquid-crystal tunable filter.

47. A method of determining the amount of a single fluorophore or a combination of fluorophores selected from a plurality of fluorophores associated with a pixel, each of the fluorophores having characterizing emission spectrum and specifying emission peak, the method comprising the steps of:

(a) providing a plurality of wide-band emission filters;

(b) recording emitted light intensity as retrieved after passing through each one of said plurality of emission filters, such that the pixel is representable by a vector of a plurality of dimensions, the number of dimensions being equal to the number of plurality of wide-band emission filters;

(c) using an algorithm for evaluating the amount of each of the plurality of fluorophores associated with the pixel.

48. A method of determining the amount of a single fluorophore or a combination of fluorophores selected from a plurality of fluorophores associated with a pixel, each of the fluorophores having characterizing excitation and emission spectra and specifying excitation and emission peaks, the method comprising the steps of:

(a) providing a plurality of pairs of wide-band excitation filters and wide-band emission filters;

(b) exciting fluorophores of the pixel with light filtered through one of said wide-band excitation filters, and recording emitted light intensity as retrieved after passing through its paired emission filter;

(c) repeating step (b) for all of said plurality of pairs of filters, such that the pixel is representable by a vector of a plurality of dimensions, the number of dimensions being equal to the number of said plurality of pairs of filters; and (d) using an algorithm for evaluating the amount of each of the plurality of fluorophores associated with the pixel.

49. An apparatus far determining the amount of a single fluorophore or a combination of fluorophores selected from a plurality of fluorophores associated with a pixel, each of the fluorophores having characterizing excitation and emission spectra and specifying excitation and emission peaks, the apparatus comprising:

(a) a light source;

(b) a plurality of pairs of wide-band excitation filters and wide-band emission filters;

(c) a control device for:
  (i) selecting a pair of said plurality of pairs;
  (ii) exciting fluorophores of the pixel with light originating from said light source filtered through one of said wide-band excitation filters; and
  (iii) repeating steps (i)–(ii) for all of said plurality of pairs of filters, such that the pixel is representable by a vector of a plurality of dimensions, the number of dimensions being equal to the number of said plurality of pairs of filters;

(d) a light recording device for recording emitted light intensity as retrieved after passing through said emission filters; and (e) a computing device including an algorithm for evaluating the amount of each of the plurality of fluorophores associated with the pixel.

* * * * *

UNITED STATES PATENT AND TRADEMARK OFFICE
CERTIFICATE OF CORRECTION

PATENT NO. : 5,834,203
DATED : November 10, 1998
INVENTOR(S) : Katzir et al.

It is certified that error appears in the above-identified patent and that said Letters Patent is hereby corrected as shown below:

<u>Title page,</u>
Item [54], Title should be changed from:

"METHOD FOR CLASSIFICATION OF PIXELS INTO GROUPS ACCORDING TO THEIR SPECTRA USING A PLURALITY OF WIDE BAND FILTERS AND HARDWIRE THEREFORE"

to read:

-- METHOD FOR CLASSIFICATION OF PIXELS INTO GROUPS ACCORDING TO THEIR SPECTRA USING A PLURALITY OF WIDE BAND FILTERS AND HARDWARE THEREFORE --

Signed and Sealed this

Twenty-sixth Day of February, 2002

*Attest:*

*Attesting Officer*

JAMES E. ROGAN
*Director of the United States Patent and Trademark Office*